(12) United States Patent
Casar et al.

(10) Patent No.: US 9,359,385 B2
(45) Date of Patent: Jun. 7, 2016

(54) PREPARATION OF SITAGLIPTIN INTERMEDIATES

(75) Inventors: Zdenko Casar, Ljubljana (SI); Gaj Stavber, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 139 days.

(21) Appl. No.: 14/122,540

(22) PCT Filed: May 25, 2012

(86) PCT No.: PCT/EP2012/059802
§ 371 (c)(1),
(2), (4) Date: Mar. 20, 2014

(87) PCT Pub. No.: WO2012/163815
PCT Pub. Date: Dec. 6, 2012

(65) Prior Publication Data
US 2014/0187558 A1    Jul. 3, 2014

(30) Foreign Application Priority Data
May 27, 2011    (EP) ..................................... 1167798

(51) Int. Cl.
| | | |
|---|---|---|
| *C07F 7/10* | (2006.01) | |
| *C07F 7/08* | (2006.01) | |
| *C07C 227/06* | (2006.01) | |
| *C07C 269/06* | (2006.01) | |
| *C07C 303/40* | (2006.01) | |
| *C07D 487/04* | (2006.01) | |
| *C07C 239/20* | (2006.01) | |

(52) U.S. Cl.
CPC ................. *C07F 7/10* (2013.01); *C07C 227/06* (2013.01); *C07C 239/20* (2013.01); *C07C 269/06* (2013.01); *C07C 303/40* (2013.01); *C07D 487/04* (2013.01); *C07F 7/0892* (2013.01)

(58) Field of Classification Search
CPC .. C07C 227/06; C07C 239/20; C07C 269/06; C07C 303/40; C07D 487/04; C07F 7/0892; C07F 7/10
See application file for complete search history.

(56) References Cited

FOREIGN PATENT DOCUMENTS

WO        WO03/004498        *    1/2003

OTHER PUBLICATIONS

Xu et al., "Transition-Metal-Based Lewis Acid Catalysis of Aza-type Michael Additions of Amines to alpha, beta-Unsaturated Electrophiles in Water," Helvetica Chimica Acta—vol. 87, 2004, 1522-1526.*
Ranu et al., "Solvent-free, catalyst-free Michael-type addition of amines to electron-deficient alkenes," ARIVOC 2002(vii) 76-81.*
Mukherjee et al., "Aza-Michael addition of amines to activated alkenes catalyzed by Silica supported perchloric acid under solvent-free condition," Letters in Organic Chemistry (2007), 4, 54-59.*
Firouzabadi et al., "Micellar Solution of Sodium Dodecyl Sulfate (SDS) Catalyzes Facile Michael Addition of Amines and Thiols to alpha, beta-unsaturated Ketones in Water under Neutral Conditions," Adv. Synth. Catal. 2005, 347, 655-661.*
Scettri et al., "Organocatalytic asymmetric aza-Michael addition of aniline to chalcones under solvent-free conditions," Tetrahedron: Asymmetry, 19 (2008) 2149-2152.*
Feng, et al., "The asymmetric synthesis of Sitagliptin, a selective dipeptidyl peptidase IV inhibitor for the treatment of type 2 diabetes," Journal of Chemical Research, Science Reviews Ltd., Apr. 1, 2010, pp. 230-232, vol. 34, GB.
International Search Report, European Patent Application No. PCT/EP2012/059802 dated Sep. 3, 2012.

* cited by examiner

*Primary Examiner* — Paul A Zucker
*Assistant Examiner* — Mark Luderer
(74) *Attorney, Agent, or Firm* — Arent Fox LLP

(57) ABSTRACT

The invention relates to the preparation of chiral compounds, in particular to the preparation of chiral compounds which may be used as intermediates for the preparation of antidiabetic agents, preferably sitagliptin.

13 Claims, No Drawings

PREPARATION OF SITAGLIPTIN INTERMEDIATES

CROSS-REFERENCE TO RELATED APPLICATION

This application is a National Stage entry of International Application No. PCT/EP2012/059802, filed May 25, 2012, which claims priority to European Application No. 11167798.5, filed May 27, 2011, the entire specifications, claims and drawings of which are incorporated herewith by reference.

FIELD OF THE INVENTION

The present invention relates to the preparation of chiral compounds, in particular to the preparation of chiral compounds which may be used as intermediates for the preparation of anti-diabetic agents, preferably sitagliptin.

BACKGROUND PRIOR ART

Type II diabetes mellitus (T2DM) is a global epidemic. Therefore, the research is oriented in the development of selective inhibitors of the enzyme DPP-IV as a promising new treatment for the type II diabetes.

Sitagliptin (CAS Registry Number 486460-32-6. IUPAC Name: (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amin) is an anti-diabetic agent and a potent inhibitor of the DPP-IV. It is represented by the structure:

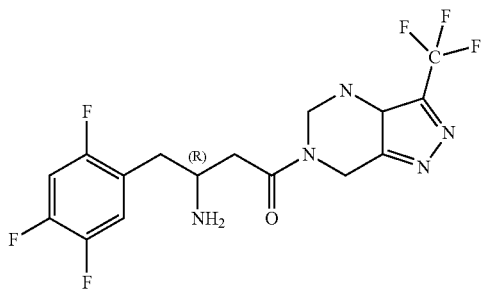

There is a constant search for improved synthetic protocols for key intermediates, in particular β-amino acid intermediates of the formula I,

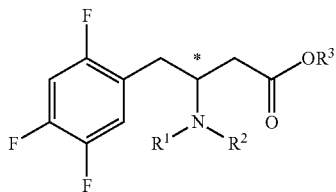

for the synthesis of sitagliptin.

WO 03/004498 disclose a method for producing the carboxylic acid of the β-amino acid intermediate of the formula I, which is performed through a 2,3,5-trifluorobenzylbromide intermediate, where enantioselectivity was induced by the use of unusual dihydropyrazine chiral auxiliaries. In the last steps, diazomethane, which is an explosive reagent, and stoichoimetric amounts of silver salts are included in the synthetic protocol which are very expensive and therefore unsuitable reagents for industrial synthesis.

Other synthetic approaches include asymmetric hydrogenation of β-enamino acid intermediates. The asymmetric hydrogenation reactions are conducted in the presence of expensive metal catalysts like rhodium in combination with chiral phosphine/diphosphine ligands (WO 03/004498, Kubryl, M.; et. al. *Tetrahedron Asymmetry* 2006, 17, 205-209.). In some cases also expensive ruthenium metal catalysts are used (WO 09/064476, WO 04/085378, WO 05/097733, WO 06/081151, Hsiao, Y.; et. al. *J. Am. Chem. Soc.,* 2004, 126, 9918-9919.). Hydrogenation with cheaper achiral catalysts involving a chiral derivatisation of enamines is also known (WO 04/085661).

Also known are synthetic strategies, which are based on the chemocatalytic selective reduction of 3-keto esters in the presence of ruthenium or rhodium diphosphine chiral catalysts (WO 04/087650, US 2009/0192326; US 2006/0052382; Hansen, K. B.; et. al. *J. Am. Chem. Soc.* 2009, 131, 8798-8804.; Hansen K. B.; et. al. *Org. Process Res. Dev.* 2005, 9, 634-639.).

WO 09/045507 discloses a biocatalytic approach to sitagliptin where an enantioselective step was performed using an appropriate enzymes (ketoreductase) for the asymmetric reduction of the β-carbonyl part of the molecule to form than the β-hydroxy intermediates. The transformation of the obtained chiral hydroxyl intermediates to the final sitagliptin precursors was performed via azetidinone intermediates. It is well known that this step is very difficult to establish. Disadvantages of these protocols are also: reactions at high pressures (250 psi), the use of very expensive metal chiral catalysts (Rh or Ru), low stereoselectivity and product contamination with rhodium and consequently hard purification protocols of final compound.

It has been also shown that rhodium or ruthenium asymmetric catalytic hydrogenation of β-keto esters through enamines can be replaced by the an efficient biocatalytic process using special enzymes transaminases, which improve the efficiency of sitagliptin manufacturing up to 99.95% enantiomeric excess (Savile, C. K.; et. al. *Science* 2010, 329, 305-309 and references cited therein). This enzymatic route features direct amination of the prochiral sitagliptin ketone to provide the enantiopure sitagliptin, followed by phosphate salt formation to provide the final sitagliptin phosphate. It is well known that enzymatic reactions offer an environmentally friendly approach to the synthesis of final molecules but on the other hand the availability and especially price of special enzymes (isolation protocols etc.) represent a inconsiderable disadvantage of a biocatalytic process. WO 09/045507 discloses protocols for the synthesis of a β-hydroxy intermediate and the β-amino acid intermediate of formula I.

There is also disclosed an intermediate of the formula II

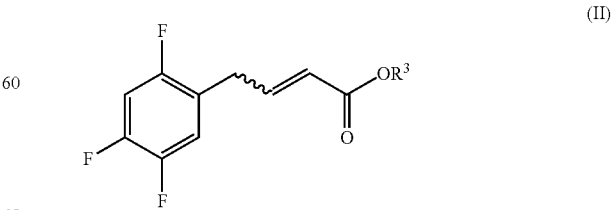

with $R^3$ being methyl, but no experimental procedure, no evidence and any other signs are devoted to this intermediate (WO 2010/122578). All synthetic strategies disclosed (WO 2010/122578) are experimentally complicated, involve relatively many synthetic steps and some of them are conducted under extreme reaction conditions (temperature up to −50° C.; dry conditions etc.). The efficiency and especially the selectivity of some individual synthetic steps are modest and consequently influence the lower overall yields of the process.

Liu et al. discloses an asymmetric synthesis of sitagliptin over 9-10 steps, with the overall 31% yield and 99.5% enantiomeric excess (Liu, F.; et. al. *J. Chem. Res.* 2010, 34, 230-232.). The synthetic strategy involving also an intermediate of formula II presents an efficient and high selective approach to sitagliptin but on the other hand offers also a lot of disadvantages. One of these disadvantages is the long and complicated 5 steps process to obtain the intermediate of the formula II.

Some other important disadvantages are: some steps are conducted under extreme conditions (−78° C.) where special equipment is also needed; the use of extremely hazardous reagents like BuLi strongly needed for performing the aza-Michael reaction under these conditions; some steps include $CH_2Cl_2$ as an volatile, toxic and especially non-industrial and non-environmentally friendly reaction medium;

Therefore, it was an object of the present invention to provide an improved, simple, cost-beneficial, industrial friendlier and environmentally friendly process for the preparation of an intermediate of formula I.

It was another object of the present invention to provide an improved process for the preparation of an intermediate of formula I starting from the intermediate of the formula II.

It was yet another object of the present invention to provide new intermediates suitable for the preparation of anti-diabetic agents, preferably sitagliptin.

SUMMARY OF THE INVENTION

The present invention relates to a process for the preparation of an intermediate of formula I

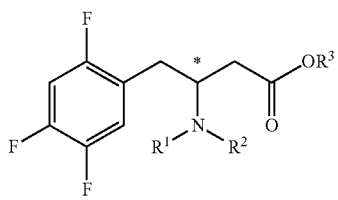

(I)

wherein the stereogenic center marked with an * is either in (R)- or (S)-configuration at marked center, or it is in racemic form, and
wherein $R^1$ and $R^2$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted;
(ix) alkoxycarbonyl residues optionally chiral, having from 2 to 13 carbon atoms;
(x) aryloxycarbonyl residues optionally chiral, having from 7 to 25 carbon atoms;
(xi) tosyl;
(xii) silyl residues optionally chiral, having from 3 to 15 carbon atoms; and
(xiii) silyloxy residues optionally chiral, having from 3 to 15 carbon atoms;
wherein $R^3$ is selected from alkyl residues having from 1 to 6 carbon atoms;
the process comprising the steps of:
(a) providing an intermediate of formula II,

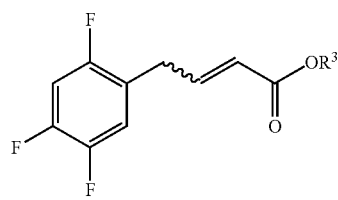

(II)

(b) reacting the intermediate of formula II with an amine of formula III $HNR^1R^2$ (III)

wherein $R^1$ and $R^2$ are as defined above, in a protic solvent, particularly in water; or in a mixture of protic solvents, wherein the mixture particularly comprises water; or without adding of solvents in step (b); to obtain an intermediate of formula I.

The present invention represents an improvement over the known methodologies. The developed reactions are conducted under mild reaction conditions; simple, non-hazardous and the commercially available reagents may be used; reactions are performed under environmentally friendly reaction conditions using water as a "green" solvent or using no solvent at all; there is no need for special equipment for efficiency of the process; and much less reaction steps considering previous patents and literature are necessary to obtain an intermediate of formula.

Other aspects and further preferred embodiments are set out as defined in the claims and in the detailed description of the invention.

DEFINITIONS

The term "intermediate" as used herein shall be understood as including compounds which are isolated from a reaction mixture and compounds which are not isolated from a reaction mixture.

The term "room temperature" or "ambient temperature" used herein will be understood by the person skilled in the art as referring to a temperature between about 20° C. and about 30° C., particularly between 20° C. and 30° C.

The term "without adding of solvents" used herein is meant to refer to conditions in which no solvent or solvents are added additionally to the reactants, particularly in which no solvent or solvents are added additionally to any adducts, and if present, any catalysts, any ligands, any bases, any acids, any organocatalysts, any promoters, and any surfactants. Thus, the step (b) of the process as defined below is essentially carried out in the absence of a solvent or solvents. In the event that one or more reactant, particularly an adduct, a catalyst, a ligand, a base, an acid, an organocatalyst, a promoter, or a surfactant, could be considered as solvent, the term "without adding of solvents" used herein is meant to refer to conditions in which no solvent or solvents are additionally added in step (b) of the process as defined below.

The stereogenic center marked with an * is either in (R)- or (S)-configuration at marked center, or it is in racemic form.

DETAILED DESCRIPTION OF THE INVENTION

Process for the Preparation of an Intermediate of Formula I

According to one aspect the present invention relates to a process for the preparation of an intermediate of formula I

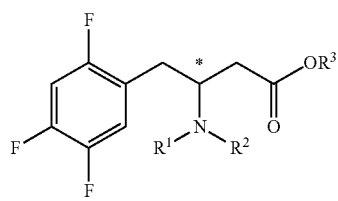
(I)

wherein the stereogenic center marked with an * is either in (R)- or (S)-configuration at marked center, or it is in racemic form, and wherein $R^1$ and $R^2$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted;
(ix) alkoxycarbonyl residues optionally chiral, having from 2 to 13 carbon atoms;
(x) aryloxycarbonyl residues optionally chiral, having from 7 to 25 carbon atoms;
(xi) tosyl;
(xii) silyl residues optionally chiral, having from 3 to 15 carbon atoms; and
(xiii) silyloxy residues optionally chiral, having from 3 to 15 carbon atoms;

wherein $R^3$ is selected from alkyl residues having from 1 to 6 carbon atoms;
the process comprising the steps of:
(a) providing an intermediate of formula II,

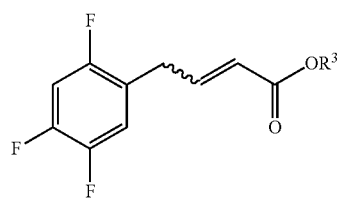
(II)

(b) reacting the intermediate of formula II with an amine of formula III $HNR^1R^2$ (III)

wherein $R^1$ and $R^2$ are as defined above, in a protic solvent, particularly in water; or in a mixture of protic solvents, wherein the mixture particularly comprises water; or without adding of solvents in step (b);
to obtain an intermediate of formula I.

In a preferred embodiment, in step (b) the solvent is selected from water, methanol, ethanol, iso-propanol, tert-butanol, trifluoroethanol, hexafluoro-2-propanol, amyl alcohol and any combination thereof, and is particularly water.

In another preferred embodiment step (b) is carried out without adding solvents.

In another preferred embodiment, step (b) is carried out at a temperature of 20° C. to 100° C., preferably of 20° C. to 85° C.

In a particularly preferred embodiment, $R^1$ and $R^2$ are identical, and are selected from
(i) hydrogen;
(ii) alkyl residues optionally chiral, having from 1 to 12 carbon atoms, wherein the alkyl residues are optionally aryl and/or aryloxy substituted;
(iii) aryl residues optionally chiral, having from 6 to 24 carbon atoms, wherein the aryl residues are optionally alkyl and/or alkyloxy substituted;
(iv) benzyl;
(v) alkoxycarbonyl residues optionally chiral, having from 2 to 13 carbon atoms;
(vi) aryloxycarbonyl residues optionally chiral, having from 7 to 25 carbon atoms;
(vii) silyl residues optionally chiral, having from 3 to 15 carbon atoms.

In a particularly preferred embodiment, $R^1$ and $R^2$ are hydrogen. In another particularly preferred embodiment, $R^1$ and $R^2$ are methyl. In still another particularly preferred embodiment, $R^1$ and $R^2$ are N-α-methylbenzyl. In another $R^2$ particularly preferred embodiment $R^1$ and R are trimethylsilyl.

In another particularly preferred embodiment, $R^1$ and $R^2$ are different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;

(v) aryloxy residues optionally chiral, having from 6 to 24 carbon atoms, wherein the aryloxy residues are optionally alkyl substituted;

(vi) benzyl;

(vii) alkaloyl residues optionally chiral, having from 2 to 13 carbon atoms, wherein the alkaloyl residues are optionally aryl substituted;

(viii) aroyl residues optionally chiral, having from 7 to 25 carbon atoms, wherein the aryloxy residues are optionally alkyl substituted;

(ix) alkoxycarbonyl residues optionally chiral, having from 2 to 13 carbon atoms;

(x) aryloxycarbonyl residues optionally chiral, having from 7 to 25 carbon atoms; and (xi) tosyl;

(xii) silyl residues optionally chiral, having from 3 to 15 carbon atoms; and (xiii) silyloxy residues optionally chiral, having from 3 to 15 carbon atoms.

In a particularly preferred embodiment $R^1$ is hydrogen and $R^2$ is tosyl. In another particularly preferred embodiment $R^1$ is hydrogen and $R^2$ is benzyl. In a particularly preferred embodiment $R^1$ is hydrogen and $R^2$ is N-α-methylbenzyl. In still another particularly preferred embodiment $R^1$ is benzyl and $R^2$ is N-α-methylbenzyl. In another particularly preferred embodiment $R^1$ is benzyl and $R^2$ is N-benzyl-1-phenethyl. In a further particularly preferred embodiment $R^1$ is hydrogen and $R^2$ is O-benzyl. In another particularly preferred embodiment $R^1$ is hydrogen and $R^2$ is O-methyl. In another particularly preferred embodiment $R^1$ is hydrogen and $R^2$ is tert-butyl-oxy-carbonyl or benzyl-oxy-carbonyl. In a further particularly preferred embodiment $R^1$ is hydrogen and $R^2$ is methoxy-phenyl. In a further particularly preferred embodiment $R^1$ is hydrogen and $R^2$ is O-phenyl. In another particularly preferred embodiment $R^1$ is hydrogen and $R^2$ is O-trimethylsilyl.

The chiral aryl residues defined for the intermediate of formula I are selected from N-α-methylbenzyl, N-bis[α-methylbenzyl], N-α-ethyl-naphthyl, 2-methoxybenzyl-1-phenylethyl, 3,4-dimethoxybenzyl-1-phenylethyl, and N-benzyl-1-phenethyl In the intermediate of formula I and the intermediate of formula II, $R^3$ is typically selected from methyl, ethyl, propyl, cyclopropyl, butyl, pentyl, hexyl, isopropyl, isopentyl, tert-butyl, and is particularly methyl. In a particularly preferred embodiment $R^3$ of the intermediate of formula II is methyl (intermediate of formula IIa).

In particularly preferred embodiments, the intermediate of formula I is

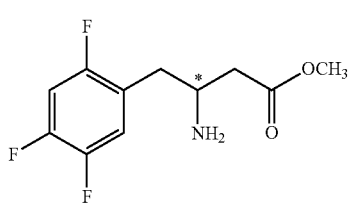
(Ia)

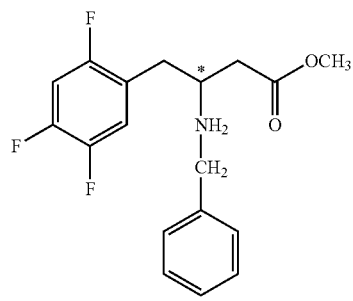
(Ib)

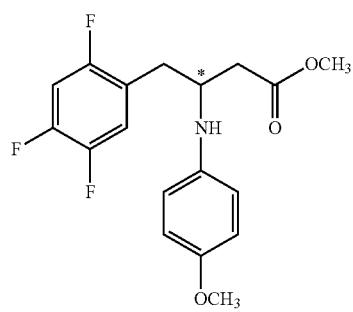
(Ic)

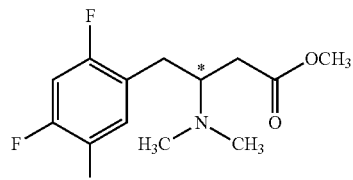
(Id)

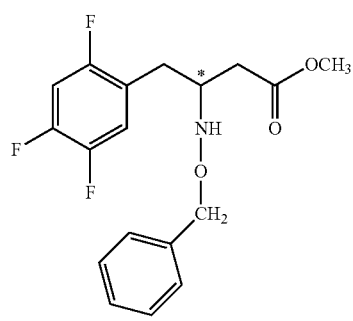
(Ie)

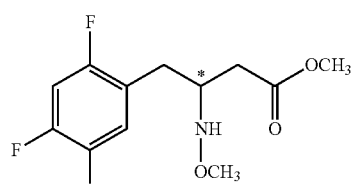
(If)

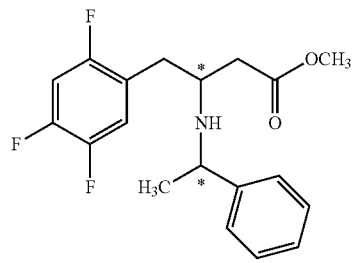
(Ig)

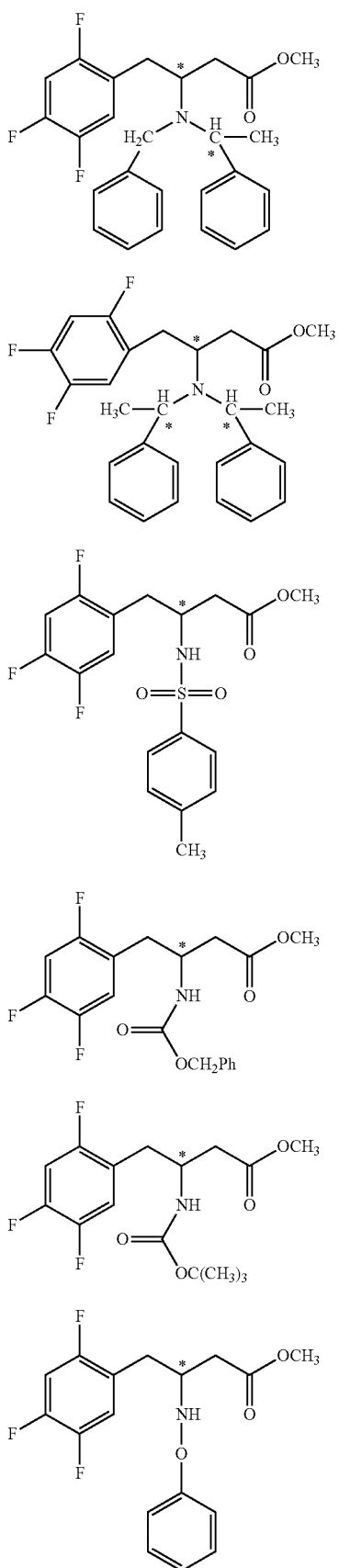

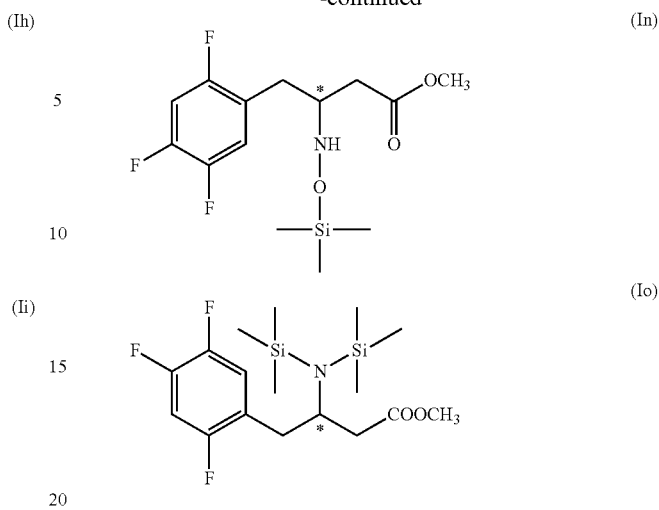

wherein the stereogenic center marked with an * is either in (R)- or (S)-configuration at marked center, or it is in racemic form.

The amine of formula III is typically selected from ammonia, an alkyl amine, an aryl amine, an alkyl-aryl amine, a silyl amine, and a silyloxy amine.

Typically, when the amine is an alkyl amine it is selected from dimethylamine, tert-butyl-carbamate and O-methylhydroxylamine. Typically, when the amine is an aryl amine it is selected from benzylamine, p-methoxybenzylamine, 3,4-dimethoxybenzylamine, p-methoxyaniline, tosylamine, benzyl carbamate dibenzylamine, naphthylamine, O-benzylhydroxylamine, O-phenylhydroxylamine and benzhydrylamine. Typically, when the amine is an alkyl-aryl amine it is selected from methyl-phenyl-amine, N-α-methyl-benzylamine, N-bis-[α-methylbenzylamine], and N-benzyl-1-phenylethyl. Typically, when the amine is a silyl amine it is selected from hexamethyldisilazane, potassium bis(trimethylsillyl)amide, sodium bis(trimethylsillyl)amide, lithium bis(trimethylsillyl)amide, 1,1,3,3-tetramethyldisilazane and 1,1,3,3-tetramethyl-1,3-diphenylsilazane. Typically, when the amine is a silyloxy amine it is selected from O-(trimethylsilyl)hydroxylamine, and N,O-bis(trimethylsillyl)hydroxylamine.

In preferred embodiment, the amine in step (b) is present in an amount of 1.0 to 2.0 equivalents, particularly 1.1 to 2.0, preferably about 1.2 to 1.7 equivalents, with respect to the intermediate of formula II.

In a further preferred embodiment, the reaction time in step (b) is between 5 to 52 hours, particularly between 6 to 48 hours.

In one embodiment, step (b) is a non-catalyzed process. Typically, when step (b) is carried out in a protic solvent or in a mixture of protic solvents, step (b) is then carried out at a temperature of 50° C. to 90° C., preferably of 60° C. to 85° C., and more preferably about 60° C. Typically, when step (b) is carried out in a protic solvent or in a mixture of protic solvents, the reaction time is between 10 to 30 hours, preferably about 16 hours, when step (b) is a non-catalyzed process.

Typically, when step (b) is a non-catalyzed process, and when step (b) is carried out without adding of solvents, step (b) is then carried out at a temperature of 25° C. to 90° C., preferably of 60° C. to 85° C., and more preferably about 70° C. Typically, when step (b) is carried out without adding of solvents, the reaction time is between 8 to 20 hours, preferably about 12 hours, when step (b) is a non-catalyzed process.

In another embodiment, when step (b) is carried out in a protic solvent or in a mixture of protic solvents, step (b) is a transition metal catalyzed process, particularly a transition metal catalyzed process using a catalyst comprising a transition metal compound, and optionally at least one ligand. Typically, the transition metal compound is selected from copper compounds, indium compounds, zinc compounds, iron compounds, manganese compounds, cerium compounds, bismuth compounds, scandium compounds, ytterbium compounds, yttrium compounds, tin compounds and vanadium compounds, particularly selected from copper compounds, indium compounds, scandium compounds, ytterbium compounds and iron compounds. When the transition metal compound is a copper compound it is typically selected from copper(I) acetate, copper(I) chloride, copper (II) chloride, cooper(I) triflate, copper(II) triflate, cooper(II) acetylacetonate, cooper(II) chlorate, and any combination thereof, and is particularly selected from copper(I) acetate, copper(II) triflate, and copper(II) bromide. When the transition metal compound is an indium compound it is typically selected from indium(III) chloride, indium(II) chloride, indium(III) bromide, indium(III) perchlorate, and indium (III) nitrate, and is particularly indium(III) chloride. When the transition metal compound is a zinc compound it is typically selected from zinc(II) chloride, zinc(II) bromide, zinc(II) perchlorate, and zinc(II) oxalate, and is particularly zinc(II) chloride. When the transition metal compound is an iron compound it is typically selected from iron(II) chloride, iron (III) chloride, iron(II) acetylacetonate, iron(III) acetylacetonate, iron(III) chloride hexahydrate, iron(III) triflate, iron(III) chlorate, and iron(III) bromide, and is particularly iron(III) chloride. When the transition metal compound is a vanadium compound it is typically selected from vanadium(III) acetylacetonate, vanadium(V) oxychloride, vanadium(IV) chloride, and particularly vanadium(IV) chloride or oxychloride, and is particularly vanadium(III) acetylacetonate. When the transition metal compound is a scandium compound it is typically selected from scandium(III) triflate, scandium(III) oxalate, scandium(III) chloride, scandium(III) perchlorate, and is particularly scandium(III) triflate. When the transition metal compound is a yttrium compound it is typically selected from yttrium(III) triflate.

Typically, the transition metal compound is present in an amount of 2-25 mol %, particularly of 4-20 mol %, and more particularly about 8-15 mol % to the intermediate of formula II.

The optionally at least one ligand in the transition metal catalyzed process of step (b) is selected from monophosphine ligands, diphosphine ligands, and any combination thereof. The monophosphine ligand is typically selected from triphenylphosphine, tributylphosphine, trimethylphosphine, tricyclohexylphosphine, tri-(o-tolyl)phosphine, tri-(2-furyl)phosphine, tris(dimethylamino)phosphine, tribenzylphosphine, tripyrolydinophosphine, tris(4-methoxyphenyl)phosphine, and any combination thereof. The diphosphine ligand is typically selected from 1,2-bis(diphenyl-phosphino)benzene, 1,1,-bis(di-tert-butylphosphino)ferrocene, (oxydi-2,1-phenylene)bis-(diphenylphosphine), (R)-2,2-bis(diphenylphosphino)-1,1-binaphthalene, (S)-2,2-bis(diphenylphosphino)-1,1-binaphthale, (S,R)-(diphenylphosphino)-ferrocenyl-ethyldi-tert-butylphosphine, (R,S)-(diphenylphosphino)-ferrocenyl-ethyldi-tert-butylphosphine, and any combination thereof. Typically, the at least one ligand is present in an amount of 2-20 mol %, particularly of 4-15 mol %, and more particularly 8-10 mol %, with respect to the intermediate of formula II.

In a preferred embodiment, the transition metal catalyzed process in step (b) is optionally carried out in the presence of a base, particularly wherein the base is selected from NatOBu, KtOBu, K$_2$CO$_3$, Na$_2$CO$_3$, KOAc, NaOAc, and any combination thereof, more particularly NatOBu. Typically, the base is present in an amount of 5-25 mol %, particularly of 10-20 mol %, and more particularly about 15 mol %, with respect to the intermediate of formula II.

In another preferred embodiment, the transition metal catalyzed process in step (b) is carried out in the absence of a base.

In a particularly preferred embodiment, the transition metal catalyzed process in step (b) is carried out in the presence of a surfactant as defined below.

In another embodiment, step (b) is an acid catalyzed process. In a preferred embodiment, the acid is a Lewis acid, particularly selected from copper(II) acetate, copper(II) chloride, copper(II) triflate, iron(III) chloride, indium(III) chloride, zinc(II) chloride, scandium(III) triflate, ytterbium(III) triflate and vanadium(III) acetyacetonate. In another preferred embodiment, the acid is a Brønsted acid, particularly selected from 4-dodecylbenzenesulfonic acid (DBSA), phosphotungstic acid, phosphomolybdic acid, Nafion-H, trifluoromethanesulphonic acid (HOTf), methanesulphonic acid, p-toluenesulfonic acid (PTSA), chlorsulfonic acid, 2,5-dinitrobenzenesulfonic acid (DNBSA), sulfuric acid, polystyrenesulfonic acid (PSSA), boric acid, phenylboric acid, and any combination thereof, and is particularly DBSA, PSSA or phosphotungstic acid.

Typically, when step (b) is carried out in a protic solvent or in a mixture of protic solvents, and step (b) is an acid catalyzed process the acid then is present in an amount of 5-30 mol %, particularly of 8-25 mol %, and more particularly about 10-20 mol %, to the intermediate of formula II. Typically, when step (b) is carried out in a protic solvent or in a mixture of protic solvents, and step (b) is an acid catalyzed process step (b) is then carried out at a temperature of 25° C. to 90° C., preferably of 60° C. to 85° C., and more preferably about 60° C. to 65° C. The reaction time is typically then between 6 to 24 hours, particularly between 10 to 24 hours.

Typically, when step (b) is carried out without adding of solvents, and step (b) is an acid catalyzed process the acid then is present in an amount of 3-30 mol %, particularly of 4-25 mol %, and more particularly about 5-20 mol % to the intermediate of formula II. Typically, when step (b) is carried out without adding solvents, and step (b) is an acid catalyzed process step (b) is then carried out at a temperature of 20° C. to 90° C., preferably of 20° C. to 60° C. The reaction time is typically then between 10 to 52 hours, particularly between 12 to 48 hours.

In still another embodiment, when step (b) is carried out in a protic solvent or in a mixture of protic solvents, step (b) is an organocatalyzed process, particularly an organocatalyzed process using an optionally chiral organocatalyst. Typically, the organocatalyst is selected from amino acid chiral compounds, particularly selected from pyroglutamic acid, threonine, aspartic acid, and any combination thereof; proline derivatives; imidazolidinone derivatives; cinchona alkaloids; and tiourea derivatives. The organocatalyst is typically present in an amount of 1-30 mol %, particularly of 3-25 mol %, and more particularly 6-20 mol %, to the intermediate of formula II. The reaction time is typically between 12 to 24 hours, particularly between 15 to 20 hours, when step (b) is an organocatalyzed process. Typically, when step (b) is an organocatalyzed process, step (b) is then carried out at a temperature of 25° C. to 90° C., preferably of 60° C. to 85° C., and more preferably 60° C. to 80° C.

In a further embodiment, when step (b) is carried out in a protic solvent or in a mixture of protic solvents, step (b) is carried out in the presence of a promoter. Typically, the promoter is an organic promoter. Typically, the promoter is selected from fluorinated alcohols, in particular selected from trifluoroethanol, hexafluoro-2-propanol, and any combination thereof.

The promoter is typically present in an amount of 1-15 equivalents, particularly of 3-12 equivalents, and more particularly 5-10 equivalents, to the intermediate of formula II. When step (b) is carried out in the presence of a promoter, step (b) is typically carried out at a temperature of 25° C. to 90° C., preferably of 60° C. to 85° C., and more preferably 60° C. to 80° C. The reaction time is typically between 12 to 30 hours, particularly between 15 to 24 hours.

In still another embodiment, step (b) is carried out in the presence of a surfactant. Typically, the surfactant is selected from ionic, nonionic surfactants, and the combination thereof. When the surfactant is an ionic surfactant it is typically selected from sodium dodecyl sulfate, sodium stearate, sodium N-lauroylsarcosinate, cetyltrimethylammonium bromide, cetyltrimethylammonium chloride, benzyldodecyammonium bromide, and any combination thereof, and is particularly sodium dodecyl sulfate or cetyltrimethylammonium bromide. When the surfactant is a nonionic surfactant it is typically selected from D-α-tocopherol polyethylene glycol succinate, 4-octylphenol polyethoxylate, polyoxyethylene sorbitan monolaurate, polyethylene glycol dodecyl ether, and polyoxyethanyl-α-tocopheryl sebacate, and any combination thereof, and is particularly D-α-tocopherol polyethylene glycol succinate or polyoxyethanyl-α-tocopheryl sebacate.

When step (b) is carried out in a protic solvent or in a mixture of protic solvents, and step (b) is carried out in the presence of a surfactant, the surfactant is typically present in an amount of 0.5-30 wt %, particularly of 1-20 wt %, and more particularly 2-15 wt %, with respect to the intermediate of formula II. Typically, step (b) is carried out at a temperature of 25° C. to 90° C., preferably of 60° C. to 85° C., and more preferably 60° C. to 65° C., when it is carried out in the presence of a surfactant and in a protic solvent or in a mixture of protic solvents. Typically, the reaction time is then between 10 to 20 hours, more particularly between 15 to 20 hours.

When step (b) is carried out without adding of solvents, and step (b) is carried out in the presence of a surfactant, the surfactant is typically present in an amount of 5-40 wt %, particularly of 10-30 wt %, and more particularly 15-20 wt % with respect to the intermediate of formula II. Typically, step (b) is carried out at a temperature of 25° C. to 90° C., preferably of 60° C. to 85° C., and more preferably 60° C. to 65° C., when it is carried out in the presence of a surfactant and without adding of solvents in the step (b). Typically, the reaction time is then between 10 to 20 hours, more particularly between 16 to 18 hours.

In a particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

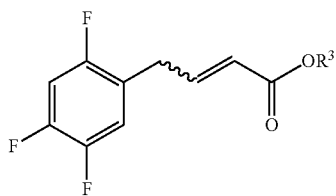

(II)

(b) reacting the intermediate of formula II with benzylamine present in an amount of 1.1 to 1.5 equivalents, preferably about 1.2 equivalents, with respect to the intermediate of formula II, in water at 20° C. to 65° C., preferably at 60° C., for 10 to 30 hours, preferably 24 hours, to obtain an intermediate of formula I.

In another particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

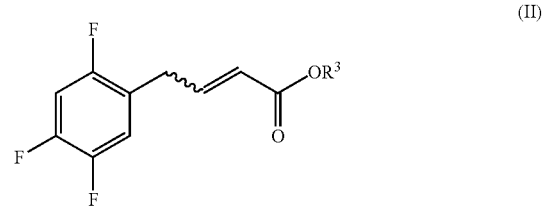

(II)

(b) reacting the intermediate of formula II with benzylamine present in an amount of 1.1 to 1.5 equivalents, preferably about 1.2 equivalents, with respect to the intermediate of formula II, in water at 30° C. for 5 to 7 hours, preferably 6 hours,
in the presence of
(i) copper(II) acetate, preferably present in an amount of 4-12 mol %, more preferably about 10 mol %, with respect to the intermediate of formula II;
(ii) triphenylphosphine, preferably present in an amount of 4-12 mol %, more preferably 8-10 mol %, with respect to the intermediate of formula II,
(iii) sodium dodecylsulfate, preferably present in an amount of 4-20 mol %, more preferably 8-10 mol %, with respect to the intermediate of formula II, and
(iv) NaOtBu, preferably present in an amount of 10-20 mol %, more preferably about 15 mol %, with respect to the intermediate of formula II,
to obtain an intermediate of formula I.

In a further particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

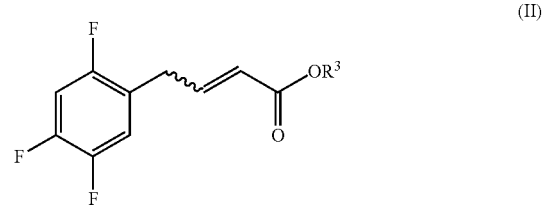

(II)

(b) reacting the intermediate of formula II with benzylamine present in an amount of 1.1 to 1.5 equivalents, preferably about 1.2 equivalents, with respect to the intermediate of formula II, in water at 30° C. to 65° C., preferably at 60° C., for 5 to 7 hours, preferably 6 hours,
in the presence of
(i) copper(II) acetate, preferably present in an amount of 4-12 mol %, more preferably about 10 mol %, with respect to the intermediate of formula II;

(ii) sodium dodecylsulfate, preferably present in an amount of 4-20 mol %, more preferably 8-10 mol %, with respect to the intermediate of formula II, and to obtain an intermediate of formula I.

In another particularly preferred embodiment in the process to obtain the intermediate of formula I, $R^1$ is hydrogen, $R^2$ is benzyl and $R^3$ is methyl; and the process comprises or consists the steps of:

(a) providing an intermediate of formula II, wherein $R^3$ is methyl;

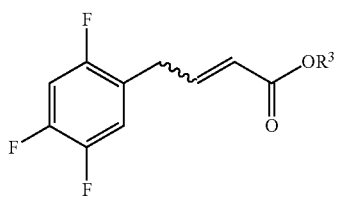

(II)

(b) reacting the intermediate of formula II with benzylamine present in an amount of 1.1 to 1.5 equivalents, preferably about 1.2 equivalents, with respect to the intermediate of formula II, in water at 50° C. to 95° C., preferably at 80° C., for 10 to 20 hours, preferably 15 hours, in the presence of (i) copper(II) bromide, preferably present in an amount of 10-20 mol %, more preferably about 15 mol %, with respect to the intermediate of formula II; or (ii) iron(III) chloride, preferably present in an amount of 10-20 mol %, more preferably about 15 mol %, with respect to the intermediate of formula II;

to obtain an intermediate of formula I.

In still another particularly preferred embodiment in the process to obtain the intermediate of formula I, $R^1$ is hydrogen, $R^2$ is benzyl and $R^3$ is methyl; and the process comprises or consists the steps of:

(a) providing an intermediate of formula II, wherein $R^3$ is methyl;

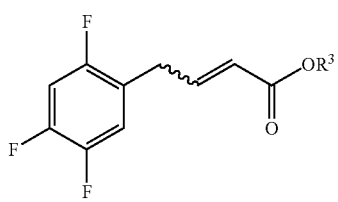

(II)

(b) reacting the intermediate of formula II with benzylamine present in an amount of 1.1 to 1.5 equivalents, preferably about 1.2 equivalents, with respect to the intermediate of formula II, in water at 25° C. to 90° C., preferably at 60° C., for 15 to 25 hours, preferably 20 hours, in the presence of indium(III) chloride, preferably present in an amount of 10-20 mol %, more preferably about 15 mol %, with respect to the intermediate of formula II;

to obtain an intermediate of formula I.

In another particularly preferred embodiment in the process to obtain the intermediate of formula I, $R^1$ is hydrogen, $R^2$ is benzyl and $R^3$ is methyl; and the process comprises or consists the steps of:

(a) providing an intermediate of formula II, wherein $R^3$ is methyl;

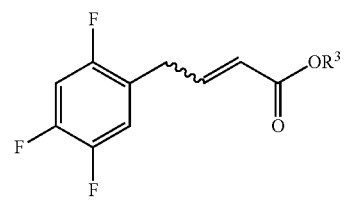

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 80° C., for 10 to 20 hours, preferably 16 hours, in the presence of (i) 2,2,2-trifluoroethanol, preferably present in an amount of 1-15 equivalents and more preferably 5-10 equivalents with respect to the intermediate of formula II;

to obtain an intermediate of formula I.

In yet another particularly preferred embodiment in the process to obtain the intermediate of formula I, $R^1$ is hydrogen, $R^2$ is benzyl and $R^3$ is methyl; and the process comprises or consists the steps of:

(a) providing an intermediate of formula II, wherein $R^3$ is methyl;

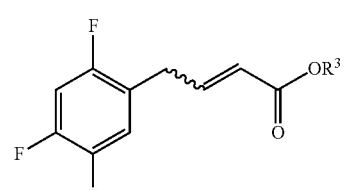

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 15 to 25 hours, preferably 20 hours, in the presence of (i) 1,1,1,3,3,3-hexafluoro-2-propanol, preferably present in an amount of 1-15 equivalents, more preferably 5-10 equivalents, with respect to the intermediate of formula II;

to obtain an intermediate of formula I.

In another particularly preferred embodiment in the process to obtain the intermediate of formula I, $R^1$ is hydrogen, $R^2$ is benzyl and $R^3$ is methyl; and the process comprises or consists the steps of:

(a) providing an intermediate of formula II, wherein $R^3$ is methyl;

(II)

[Chemical structure: 2,4,5-trifluorocinnamate ester with OR³ group]

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 20 hours, preferably 15 hours,
in the presence of
(i) D-α-tocopherol-polyethyleneglycol-succinate, preferably present in an amount of 2-15 wt % with respect to the intermediate of formula II; or
(ii) polyoxyethanyl-α-tocopheryl-sebacate, preferably present in an amount of 2-15 wt % with respect to the intermediate of formula II;
to obtain an intermediate of formula I.

In a further particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

(II)

[Chemical structure: 2,4,5-trifluorocinnamate ester with OR³ group]

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 60° C., for 15 to 25 hours, preferably 20 hours,
in the presence of
(i) sodium dodecylsulfate, preferably present in an amount of 2-15 wt % with respect to the intermediate of formula II;
to obtain an intermediate of formula I.

In still another particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

(II)

[Chemical structure: 2,4,5-trifluorocinnamate ester with OR³ group]

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 5 to 20 hours, preferably 12 hours,
in the presence of
(i) 4-dodecylbenzenesulfonic acid (DBSA), preferably present in an amount of 15-25 mol %, more preferably about 20 mol %, with respect to the intermediate of formula II;
to obtain an intermediate of formula I.

In another particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

(II)

[Chemical structure: 2,4,5-trifluorocinnamate ester with OR³ group]

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 15 hours, preferably 20 hours,
in the presence of
(i) polystyrenesulfonic acid (PSSA), preferably present in an amount of 5-15 mol %, more preferably about 10 mol %, with respect to the intermediate of formula II; to obtain an intermediate of formula I.

In a further particularly preferred embodiment in the process to obtain the intermediate of formula I, $R^1$ is hydrogen, $R^2$ is benzyl and $R^3$ is methyl; and
the process comprises or consists the steps of:
(a) providing an intermediate of formula II, wherein $R^3$ is methyl;

(II)

[Chemical structure: 2,4,5-trifluorocinnamate ester with OR³ group]

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 25 hours, preferably 15 hours,
in the presence of
(i) phosphotungstic acid, preferably present in an amount of 5-15 mol %, more preferably about 10 mol %, with respect to the intermediate of formula II;
to obtain an intermediate of formula I.

In yet another particularly preferred embodiment in the process to obtain the intermediate of formula I, $R^1$ is hydrogen, $R^2$ is benzyl and $R^3$ is methyl; and the process comprises or consists the steps of:
(a) providing an intermediate of formula II, wherein $R^3$ is methyl;

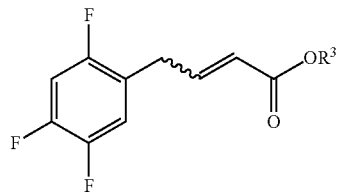

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 25 hours, preferably 18 hours,
in the presence of
(i) acid activator Nafion NR50, preferably present in an amount of 5-15 mol %, more preferably about 10 mol %, with respect to the intermediate of formula II;
to obtain an intermediate of formula I.

In a further particularly preferred embodiment in the process to obtain the intermediate of formula I, $R^1$ is hydrogen, $R^2$ is benzyl and $R^3$ is methyl; and the process comprises or consists the steps of:
(a) providing an intermediate of formula II, wherein $R^3$ is methyl;

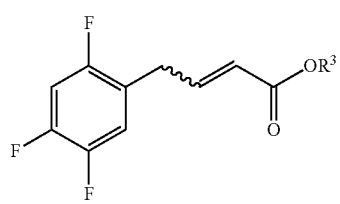

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 70° C., for 8 to 20 hours, preferably 12 hours, to obtain an intermediate of formula I.

In another particularly preferred embodiment in the process to obtain the intermediate of formula I, $R^1$ is hydrogen, $R^2$ is benzyl and $R^3$ is methyl; and the process comprises or consists the steps of:
(a) providing an intermediate of formula II, wherein $R^3$ is methyl;

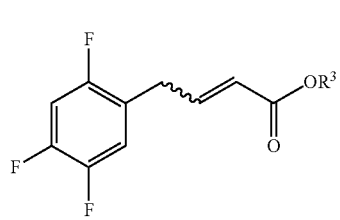

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 50° C., preferably at ambient temperature, for 24 to 52 hours, preferably 48 hours,
in the presence of
(i) 4-dodecylbenzenesulfonic acid (DBSA), preferably present in an amount of 15-25 mol %, more preferably about 20 mol %, with respect to the intermediate of formula II; to obtain an intermediate of formula I.

In yet another particularly preferred embodiment in the process to obtain the intermediate of formula I, $R^1$ is hydrogen, $R^2$ is benzyl and $R^3$ is methyl; and the process comprises or consists the steps of:
(a) providing an intermediate of formula II, wherein $R^3$ is methyl;

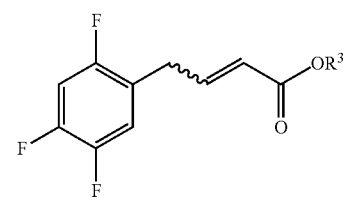

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 60° C., for 10 to 25 hours, preferably 18 hours,
in the presence of
(i) phosphotungstic acid, preferably present in an amount of 3-10 mol %, more preferably about 5 mol %, with respect to the intermediate of formula II;
to obtain an intermediate of formula I.

In a further particularly preferred embodiment in the process to obtain the intermediate of formula I, $R^1$ is hydrogen, $R^2$ is benzyl and $R^3$ is methyl; and the process comprises or consists the steps of:
(a) providing an intermediate of formula II, wherein $R^3$ is methyl;

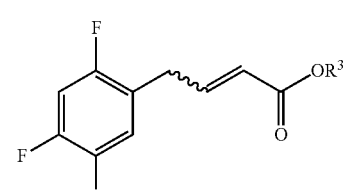

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 60° C., for 10 to 48 hours, preferably 16 hours,
in the presence of
(i) sodium dodecylsulfate preferably present in an amount of 10-30 mol %, more preferably about 20 mol %, with respect to the intermediate of formula II,
to obtain an intermediate of formula I.

In another particularly preferred embodiment in the process to obtain the intermediate of formula I, $R^1$ is hydrogen, $R^2$ is benzyl and $R^3$ is methyl; and the process comprises or consists the steps of:
(a) providing an intermediate of formula II, wherein $R^3$ is methyl;

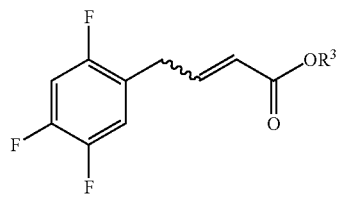
(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 60° C., for 10 to 48 hours, preferably 18 hours, in the presence of (i) cetyltrimethylammonium bromide, preferably present in an amount of 10-30 mol %, more preferably about 20 mol %, with respect to the intermediate of formula II, to obtain an intermediate of formula I.

In a further particularly preferred embodiment in the process to obtain the intermediate of formula I, $R^1$ is hydrogen, $R^2$ is O-benzyl and $R^3$ is methyl; and the process comprises or consists the steps of:
(a) providing an intermediate of formula II, wherein $R^3$ is methyl;

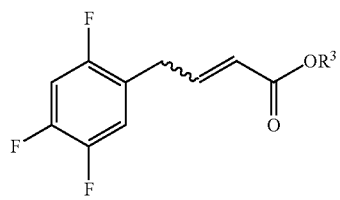
(II)

(b) reacting the intermediate of formula II with O-benzylhydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) 4-dodecylbenzenesulfonic acid (DBSA), preferably present in an amount of 15-25 mol %, more preferably about 20 mol %, with respect to the intermediate of formula II;

to obtain an intermediate of formula I.

In another particularly preferred embodiment in the process to obtain the intermediate of formula I, $R^1$ is hydrogen, $R^2$ is O-benzyl and $R^3$ is methyl; and the process comprises or consists the steps of:
(a) providing an intermediate of formula II, wherein $R^3$ is methyl;

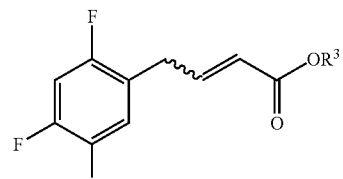
(II)

(b) reacting the intermediate of formula II with O-benzylhydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) 2,2,2-trifluoroethanol, preferably present in an amount of 1-15 equivalents, preferably 3-12 equivalents, and more preferably 5 equivalents with respect to the intermediate of formula II; to obtain an intermediate of formula I.

In another particularly preferred embodiment in the process to obtain the intermediate of formula I, $R^1$ is hydrogen, $R^2$ is O-benzyl and $R^3$ is methyl; and the process comprises or consists the steps of:
(a) providing an intermediate of formula II, wherein $R^3$ is methyl;

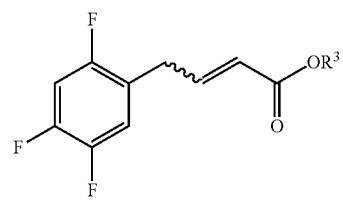
(II)

(b) reacting the intermediate of formula II with O-benzylhydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) scandium(III) triflate, present in an amount of 1-30 mol %, preferably about 5-25 mol %, more preferably about 20 mol %, with respect to the intermediate of formula II; and (ii) sodium dodecylsulfate, present in an amount of 1-30 mol %, preferably about 5-25 mol %, more preferably about 20 mol %, with respect to the intermediate of II;

to obtain an intermediate of formula I.

In another particularly preferred embodiment in the process to obtain the intermediate of formula I, $R^1$ is hydrogen, $R^2$ is O-benzyl and $R^3$ is methyl; and the process comprises or consists the steps of:
(a) providing an intermediate of formula II, wherein $R^3$ is methyl;

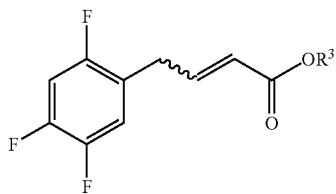

(II)

(b) reacting the intermediate of formula II with O-benzyl-hydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours,
in the presence of
(i) 2,2,2-trifluoroethanol, present in an amount of 1-15 equivalents, preferably about 3-12 equivalents, more preferably about 5 equivalents, with respect to the intermediate of formula II; and
(ii) sodium dodecylsulfate, preferably present in an amount of 1-30 mol %, preferably about 5-20 mol %, more preferably about 8 mol %, with respect to the intermediate of II;
to obtain an intermediate of formula I.

According to another aspect, there is also provided the use of a process as defined above to obtain an intermediate of formula I in a process for the preparation of anti-diabetic agents, in particular (R)-3-amino-1-[3-(trifluormethyl)-5,6,7,8-tetrahydro[1,2,4]triazol[4,3-a]pyrazin-7-yl]-4-(2,4,5-trifluorphenyl)butan-1-on.

The invention will be more fully understood by references to the following examples. They should not, however, be construed as limiting the scope of the invention. The disclosure of all literature and patent citations mentioned herein are expressly incorporated by reference.

EXAMPLES

Example 1

Synthesis of methyl(E)-4-(2,4,5-trifluorophenyl)-but-2-enoate (IIa) by cobalt Catalyzed Cross-Coupling Process A dry and nitrogen-flushed 200 mL two-necked flask, equipped with a magnetic stirrer and a rubber septum was charged with anhydrous THF (20 mL) and cooled to −20° C. Afterwards 2,4,5-trifluorobenzene (65.2 mmol, 13.7 g, 7.6 mL) was initiated through a septum following by very slow addition of iPrMgCl (2 M in THF, 1.0 equiv. according to 2,4,5-trifluorobenzene, 39.6 mL). The reaction temperature was maintained at −10° C. and the reaction mixture was stirred for an hour, until Br/Mg exchange reaction was completed and 2,4,5-trifluroarylmagnesium bromide (chloride) was formed.

Into another three-necked dry flask flushed with nitrogen, were placed cobalt(II) bromide (3.76 mmol, 6 mol % according to 2,4,5-trifluorobenzene, 822 mg, 99.99% purity), TMEDA (3.76 mmol, 6 mol % according to 2,4,5-trifluorobenzene, 564 mL) and anhydrous THF (20 mL). Such reaction system was cooled to 0° C. and during intensive stirring methyl trans-4-bromo-2-butenoate (50 mmol, 8.95 g, 5.98 mL, 90% purity) was initiated through a rubber septum and reaction mixture was stirred for 30 min. Finally, freshly prepared THF solution of Grignard reagent 2,4,5-trifluoroaryl-magnesium bromide (chloride) previously cooled to −20° C., was slowly dropping for 2 hours into the reaction system and such reaction mixture was intensively stirred at 0° C. for 10-16 hours. The saturated aqueous $NH_4Cl$ solution (150 mL) was added and reaction mixture was extracted with four portions of EtOAc (300 mL). The combined organic phases were washed with brine (200 mL), dried over anhydrous $MgSO_4$ and solvent was evaporated under reduced pressure. The crude product was purified with column chromatography (Isolera; gradient elution n-hexane/EtOAc=1/10) to obtain pure liquid/oily product (IIa) (10.8 g, 93%) as determined with $^1H$, $^{19}F$ and $^{13}C$ NMR analysis.

$^1H$ NMR (500 MHz, $CDCl_3$, ppm) δ 6.90-7.05 (m, 2ArH+1H), 5.80 (dt, J=15.5 Hz, J=1.5 Hz 1H), 3.73 (s, 3H), 3.50 (d, J=6.6 Hz, 2H).

$^{13}C$ NMR (125 MHz, $CDCl_3$, ppm) δ 30.6, 51.4, 105.5 (dd, J=28.5 Hz, J=21.5 Hz), 118.1 (dd, J=19.0 Hz, J=6.0 Hz), 120.8 (m), 124.5, 145.5, 147.8 (m), 150.1 (m), 156.8 (m), 166.3 (0=0).

$^{19}F$ NMR (470 MHz, $CDCl_3$, ppm) 5-120.4 (m), −136.3 (m), −143.5 (m).

Example 2

Synthesis of methyl 3-benzylamino-4-(2,4,5-trifluorophenyl)butanoate (Ib) from (IIa) through aza-Michael Reaction in Pure Water β-Unsaturated ester methyl(E)-4-(2,4,5-trifluorophenyl)-but-2-enoate (IIa) (0.5 mmol, 115 mg) and benzylamine (0.6 mmol, 68 mg, 99% purity) were placed into a glass flask and the deionized water was added (3 mL). The heterogenic reaction mixture (aqueous dispersion) was intensively stirred (1000 rpm) at 60° C. for 16 hours. The reaction mixture was diluted with water (5 mL) and extracted with EtOAc (2×25 mL). The combined organic layers were dried over anhydrous $MgSO_4$, the organic solvent was evaporated under reduced pressure and obtained crude reaction mixture (165 mg) was analyzed with $^1H$,NMR spectroscopy. The crude product (Ib) was purified using column chromatography ($SiO_2$, hexane: ethyacetate=2:1) and brownish liquid product (Ib) (102 mg, 61% yield) was obtained. The compound methyl 3-benzylamino-4-(2,4,5-trifluorophenyl)butanoate (Ib) was confirmed also with $^{13}C$ NMR analysis and $^1H$-$^{15}N$ HMBC NMR correlation spectroscopy.

$^1H$ NMR (500 MHz, $CDCl_3$, ppm) δ 7.28 (m, 5H), 7.04 (m, 1H), 6.90 (m, 1H), 3.84 (dd, J=6.5 Hz, J=2.2 Hz, 2H), 3.67 (s, 3H), 3.25 (pentet, J=6.3 Hz, $1H_c$, $H_cC$—NH—), 2.90 (dd, J=14.0 Hz, J=6.3 Hz, $1H_a$, $H_aC$—COO—), 2.72 (dd, J=14 Hz, J=6.3 Hz, $1H_b$, $H_bC$—COO—), 2.45 (dd, J=21.0 Hz, J=6.3 Hz, 2H), 1.95 (bs, NH).

$^{13}C$ NMR (125 MHz, $CDCl_3$, ppm) δ 172.3, 156.1 (dd, J=235.0 Hz, J=1.25 Hz), 148.5 (dd, J=247.0 Hz, J=1.25 Hz), 146.5 (dd, J=267 Hz, J=15 Hz), 140.0, 128.4, 128.0, 127.0, 122.1, 119.1 (dd, J=18.75 Hz, J=5.0 Hz), 105.3 (dd, J=28.75 Hz, J=21.25 Hz), 54.4, 51.6, 51.0, 38.4, 33.0.

Example 3

Copper-catalyzed [Cu(OAc)₂] Synthesis of methyl 3-benzylamino-4-(2,4,5-trifluorophenyl)butanoate (Ib) from (IIa) Through Aza-Michael Reaction in Water in the Presence of Phosphine Ligand and Surfactant In a two-necked round bottom flask were placed $Cu(OAc)_2$ (0.11 mmol, 19.1 mg), NatOBu (0.13 mmol, 12.6 mg), $Ph_3P$ (0.11 mmol, 28.8 mg) and anionic surfactant sodium dodecylsulfate (SDS) (0.042 mmol, 12 mg) under the nitrogen. Afterwards the deionized water (3 mL) was added and the reaction mixture was vigorously stirred (900 rpm) at ambient temperature for 30 min. Than the dispersion of β-unsaturated ester methyl(E)-4-(2,4,5-trifluorophenyl)-but-2-enoate (IIa) (1 mmol) in 2 mL of deionized water was slowly added through the rubber septum into the aqueous micellar solution (final volume: 5 mL of 0.0081 M SDS aqueous solution) following by addition of benzylamine (1 mmol, 107 mg, 110 µL). Such aqueous reaction system was intensively stirred (900 rpm) at ambient temperature for 6 hours. The reaction mixture was diluted with water (5 mL), extracted with EtOAc (2×25 mL), the combined organic layers were dried over anhydrous $MgSO_4$ and solvent was evaporated under reduced pressure. The obtained crude reaction mixture was analyzed with $^1H$ NMR and purified with column chromatography ($SiO_2$, hexane:ethyl acetate=2:1) to obtain (200 mg, 60% yield). The compound methyl 3-benzylamino-4-(2,4,5-trifluorophenyl)butanoate (Ib) was confirmed also with HPLC-MS analysis.

Example 4

Copper-Catalyzed [$CuBr_2$] Synthesis of methyl 3-benzylamino-4-(2,4,5-trifluorophenyl)butanoate (Ib) from (IIa) Through Aza-Michael Reaction in Water with No Presence of any Ligand and Base In a glass round bottom flask equipped with magnetic stirrer and condenser were placed $CuBr_2$ (0.075 mmol; 15 mol % according to (IIa), 17 mg), starting material methyl (E)-4-(2,4,5-trifluorophenyl)-but-2-enoate (IIa) (0.5 mmol, 115 mg) and were well suspended in 2.5 mL of water (800 rpm). Such aqueous system was slowly heated to 80° C., than benzylamine (0.6 mmol; 1.2 equiv. according to (IIa), 66 µL) was dropped into reaction system and vigorously stirred for 15 hours. The reaction mixture was diluted with water (2.5 mL), extracted with EtOAc (2×25 mL), the combined organic layers were washed than with brine (1×30 mL) and finally dried over anhydrous $MgSO_4$. After the solvent was evaporated under reduced pressure, the obtained crude product (Ib) (154 mg; 91.5% yield) was analyzed with $^1H$ NMR analysis. The compound methyl 3-benzylamino-4-(2,4,5-trifluorophenyl)butanoate (Ib) was confirmed also with HPLC-MS analysis.

Example 5

Iron(III) chloride catalyzed synthesis of methyl 3-benzylamino-4-(2,4,5-trifluorophenyl)butanoate (Ib) from (IIa) through aza-Michael Reaction in Water In a thick-walled glass vial equipped with a magnetic stir bar were placed $FeCl_3 \times 6H_2O$ (0.075 mmol; 15 mol % according to (IIa), 21 mg), starting material methyl(E)-4-(2,4,5-trifluorophenyl)-but-2-enoate (IIa) (0.5 mmol, 115 mg) and were well suspended in 2.5 mL of water (800 rpm). Such aqueous system was slowly heated to 80° C., than benzylamine (0.6 mmol; 1.2 equiv. according to (IIa), 66 µL) was dropped into reaction system which was than vigorously stirred for 15 hours. The reaction mixture was diluted with water (2.5 mL), extracted with EtOAc (2×25 mL), the combined organic layers were washed than with brine (1×30 mL) and finally dried over anhydrous $MgSO_4$. After the solvent was evaporated under reduced pressure, the obtained crude product (Ib) (140 mg; 83% yield) was analyzed with $^1H$ NMR analysis. The compound methyl 3-benzylamino-4-(2,4,5-trifluorophenyl)butanoate (Ib) was confirmed also with HPLC-MS analysis.

Example 6

Indium(III) chloride-catalyzed synthesis of methyl 3-benzylamino-4-(2,4,5-trifluorophenyl)butanoate (Ib) from (IIa) Through Aza-Michael Reaction in Water In a thick-walled glass vial equipped with a magnetic stir bar were placed $InCl_3$ (0.075 mmol; 15 mol % according to (IIa), 16.7 mg), starting material methyl(E)-4-(2,4,5-trifluorophenyl)-but-2-enoate (IIa) (0.5 mmol, 115 mg) and were well suspended in 2.5 mL of water (800 rpm). Such aqueous system was slowly heated to 60° C., than benzylamine (0.6 mmol; 1.2 equiv. according to (IIa), 66 µL) was dropped into reaction system which was than vigorously stirred for 20 hours. The reaction mixture was diluted with water (2.5 mL), extracted with EtOAc (2×25 mL), the combined organic layers were washed than with brine (1×30 mL) and finally dried over anhydrous $MgSO_4$. After the solvent was evaporated under reduced pressure, the obtained crude product (Ib) (150 mg; 89° A yield) was analyzed with $^1H$ NMR analysis. The compound methyl 3-benzylamino-4-(2,4,5-trifluorophenyl)butanoate (Ib) was confirmed also with HPLC-MS analysis.

Example 7

Synthesis of methyl 3-benzylamino-4-(2,4,5-trifluorophenyl)butanoate (Ib) from (IIa) through aza-Michael Reaction in Water in the Presence of 2,2,2-Trifluoroethanol (TFE) as Promoter In a thick-walled glass vial equipped with a magnetic stir bar was placed methyl(E)-4-(2,4,5-trifluorophenyl)-but-2-enoate (IIa) (0.5 mmol, 115 mg) which was than vigorously stirred in 2.0 mL of water (900 rpm) to obtain well dispersed aqueous system. Afterwards 2,2,2-trifluoroethanol (5 mmol, 10 equiv. according to (IIa), 360 µL) was slowly dropped into heterogenic reaction system and slowly heated to 80° C. Finally, benzylamine (0.6 mmol, 66 µL) was slowly added and such reaction mixture was vigorously stirred (900 rpm) at 80° C. for 16 hours. Solvent TFE was first evaporated under reduced pressure, organic aqueous residue was extracted with EtOAc (2×30 mL), combined organic phases were finally washed with brine (1×40 mL) and dried over anhydrous $MgSO_4$. After the solvent was evaporated under reduced pressure, the obtained crude product (Ib) (154 mg; 91% yield) was analyzed and determined with $^1H$, $^{13}C$ NMR analysis. The compound methyl 3-benzylamino-4-(2,4,5-trifluorophenyl)butanoate (Ib) was confirmed also with HPLC-MS analysis.

Example 8

Synthesis of methyl 3-benzylamino-4-(2,4,5-trifluorophenyl)butanoate (Ib) from (IIa) through aza-Michael Reaction in Water in the Presence of 1,1,1,3,3,3-Hexafluoro-2-Propanol (HFIP) as Promoter In a thick-walled glass vial equipped with a magnetic stir bar was placed methyl(E)-4-(2,4,5-trifluorophenyl)-but-2-enoate (IIa) (0.5 mmol, 115 mg) which was than vigorously stirred in 2.0 mL of water (900 rpm) to obtain well dispersed aqueous system. Afterwards 1,1,1,3,3,3-hexafluoro-2-propanol (5 mmol, 10 equiv. according to (IIa), 526 μL) was slowly dropped into heterogenic reaction system and slowly heated to 65° C. Finally benzylamine (0.6 mmol, 66 μL) was slowly added and such reaction mixture was vigorously stirred (900 rpm) at 65° C. for 20 hours. Solvent HFIP was first evaporated under reduced pressure, organic aqueous residue was extracted with EtOAc (2×30 mL), combined organic phases were finally washed with brine (1×40 mL) and dried over anhydrous $MgSO_4$. After the solvent was evaporated under reduced pressure, the obtained crude product (Ib) (142 mg; 84% yield) was analyzed and determined with $^1H$, $^{13}C$ NMR analysis. The compound methyl 3-benzylamino-4-(2,4,5-trifluorophenyl)butanoate (Ib) was confirmed also with HPLC-MS analysis.

Example 9

Synthesis of methyl 3-benzylamino-4-(2,4,5-trifluorophenyl)butanoate (Ib) from (IIa) through aza-Michael Reaction in Water in the Presence of Non-Ionic Surfactant D-α-Tocopherol-Polyethyleneglycol-Succinate (TPGS) (Micelle-Based Aqueous System)

Starting material methyl(E)-4-(2,4,5-trifluorophenyl)-but-2-enoate (IIa) (0.5 mmol, 115 mg) was highly suspended in 3 mL of 2 wt % aqueous solution of surfactant TPGS and such reaction mixture was vigorously stirred (800 rpm) for 20 minutes. Afterwards benzylamine (0.6 mmol, 1.2 equiv., 66 μL) was slowly dropped into aqueous system (3 μL/min) and reaction mixture was heated at 65° C. for 15 hours. The reaction mixture was diluted with brine (4 mL), extracted with EtOAc (2×30 mL) and combined organic layers were dried over anhydrous $MgSO_4$. After the solvent was evaporated under reduced pressure, the obtained crude product (Ib) (150 mg; 89% yield) was analyzed and proved with $^1H$ NMR analysis. The compound methyl 3-benzylamino-4-(2,4,5-trifluorophenyl)butanoate (Ib) was confirmed also with HPLC-MS analysis.

Example 10

Synthesis of methyl 3-benzylamino-4-(2,4,5-trifluorophenyl)butanoate (Ib) from (IIa) through aza-Michael Reaction in Water in the Presence of nonionic surfactant polyoxyethanyl-α-tocopheryl-sebacate (PTS) (Micelle-Based Aqueous System)

Starting material methyl(E)-4-(2,4,5-trifluorophenyl)-but-2-enoate (IIa) (0.5 mmol, 115 mg) was highly suspended in 3 mL of aqueous solution of surfactant PTS (3 wt %) and such reaction mixture was vigorously stirred (800 rpm) for 20 minutes. Afterwards benzylamine (0.6 mmol, 1.2 equiv., 66 μL) was slowly dropped into aqueous system (3 μL/min) and reaction mixture was heated at 65° C. for 15 hours. The reaction mixture was diluted with brine (4 mL), extracted with EtOAc (2×30 mL) and combined organic layers were dried over anhydrous $MgSO_4$. After the solvent was evaporated under reduced pressure, the obtained crude product (Ib) (143 mg; 85% yield) was analyzed and confirmed with $^1H$ NMR analysis.

Example 11

Synthesis of methyl 3-benzylamino-4-(2,4,5-trifluorophenyl)butanoate (Ib) from (IIa) through aza-Michael Reaction in Water in the Presence of Ionic Surfactant Sodium Dodecysulfate (SDS) (Micelle-Based Aqueous System)

In a thick-walled glass vial equipped with a magnetic stir bar was placed methyl(E)-4-(2,4,5-trifluorophenyl)-but-2-enoate (IIa) (0.5 mmol, 115 mg) and 5 mL of aqueous solution of SDS in its concentration 0.008 M was than added. The reaction system was vigorously stirred for 20 min and afterwards benzylamine (0.6 mmol, 66 μL) was slowly added. Such aqueous mixture was heated at 60° C. during intense stirring (800 rpm) for 20 hours. The reaction mixture was diluted with water (5 mL), extracted with EtOAc (2×35 mL), the combined organic layers were dried over anhydrous $MgSO_4$ and solvent was evaporated under reduced pressure. The obtained crude product (Ib) (148 mg, 88% yield) was analyzed and confirmed with $^1H$ NMR.

Example 12

Synthesis of methyl 3-benzylamino-4-(2,4,5-trifluorophenyl)butanoate (Ib) from (IIa) through aza-Michael Reaction in Water in the Presence of Surfactant-Type Brønsted acid 4-dodecybenzenesulfonic acid (DBSA) (Acidic Micelle-Based Catalysis in Water)

In a thick-walled glass vial equipped with a magnetic stir bar was placed DBSA (0.1 mmol, 20 mol % according to (IIa), 33 mg) and dissolved in 2.5 mL of water under intensive stirring. Afterwards methyl(E)-4-(2,4,5-trifluorophenyl)-but-2-enoate (IIa) (0.5 mmol, 115 mg) was added and reaction mixture was vigorously stirred for 10 min at 65° C. Finally benzylamine (0.6 mmol, 66 μL) was slowly added and such aqueous micellar system was stirred (800 rpm) at 65° C. for 12 hours. Reaction mixture was diluted with saturated aqueous solution of $NaHCO_3$ (3.5 mL) and extracted with EtOAc (2×35 mL). The combined organic phases was finally washed with brine (1×40 mL), dried over anhydrous $Na_2SO_4$ and organic solvent was evaporated under reduced pressure. The obtained crude product (Ib) (154 mg, 91% yield) was analyzed and confirmed with $^1H$ and $^{13}C$ NMR analysis. The compound methyl 3-benzylamino-4-(2,4,5-trifluorophenyl)butanoate (Ib) was confirmed also with HPLC-MS analysis.

Example 13

Synthesis of methyl 3-benzylamino-4-(2,4,5-trifluorophenyl)butanoate (Ib) from (IIa) through aza-Michael reaction in water in the presence of polystyrenesulfonic acid (PSSA) as Brønsted acid promoter In a thick-walled glass vial equipped with a magnetic stir bar was placed PSSA (0.05 mmol, 10 mol % according to (IIa)) and dissolved in 2.0 mL of water under intensive stirring. Afterwards methyl(E)-4-(2,4,5-trifluorophenyl)-but-2-enoate (IIa) (0.5 mmol, 115 mg) was added and reaction mixture was vigorously stirred (800 rpm) for 10 min at 70° C. Finally benzylamine (0.6 mmol, 66 μL) was slowly added and such aqueous system was stirred (800 rpm) at 65° C. for 20 hours. Reaction mixture was diluted with saturated aqueous solution of $NaHCO_3$ (3.5 mL) and extracted with EtOAc (2×35 mL). The combined organic phases was finally washed with brine (1×40 mL), dried over anhydrous $Na_2SO_4$ and organic solvent was evaporated under reduced pressure. The obtained crude product (Ib) (141 mg, 83% yield) was analyzed and confirmed with $^1H$ and $^{13}C$ NMR and HPLC-MS analysis.

Example 14

Synthesis of methyl 3-benzylamino-4-(2,4,5-trifluorophenyl)butanoate (Ib) from (IIa) through aza-Michael reaction in water in the presence of phosphotungstic acid In a thick-walled glass vial equipped with a magnetic stir bar was placed methyl(E)-4-(2,4,5-trifluorophenyl)-but-2- enoate (IIa) (0.5 mmol, 115 mg) and 3 mL of water was added. Then 12-phosphotungstic acid was added (0.05 mmol, 10 mol % according to (IIa)) and reaction mixture was intensively stirred (800 rpm) for 10 min at 60° C. Finally benzylamine (0.6 mmol, 66 μL) was slowly dropped and such aqueous system was stirred (800 rpm) at 65° for 15 hours. Reaction mixture was diluted with saturated aqueous solution of NaHCO$_3$ (3.5 mL) and extracted with EtOAc (2×35 mL). The combined organic phases was finally washed with brine (1×40 mL), dried over anhydrous Na$_2$SO$_4$ and organic solvent was evaporated under reduced pressure. The obtained crude product (Ib) (135 mg, 80% yield) was analyzed and confirmed with $^1$H NMR and HPLC-MS analysis.

Example 15

Synthesis of methyl 3-benzylamino-4-(2,4,5-trifluorophenyl)butanoate (Ib) from (IIa) through aza-Michael reaction in water in the presence of acid activator Nafion NR50 as a reusable catalyst In a thick-walled glass vial equipped with a magnetic stir bar was placed methyl(E)-4-(2,4,5-trifluorophenyl)-but-2-enoate (IIa) (0.5 mmol, 115 mg) and 2.5 mL of water was added. Than acid activator Nafion NR50 (0.05 mmol, 10 mol % according to (IIa)) was added and reaction mixture was intensively stirred (800 rpm) for 10 min at 70° C. Finally benzylamine (0.6 mmol, 66 μL) was slowly dropped into aqueous system and the reaction mixture was stirred (800 rpm) at 65° C. for 18 hours. The catalyst Nafion NR50 was first gently filtered off, aqueous phase was then extracted with two portions of EtOAc (30 mL) and finally washed with an aqueous solution of NaHCO$_3$. The combined organic phases were dried over anhydrous Na$_2$SO$_4$ and organic solvent was evaporated under reduced pressure. The obtained crude product (Ib) (143 mg, 85° A, yield) was analyzed and confirmed with $^1$H and $^{13}$C NMR and HPLC-MS analysis.

Example 16

Synthesis of methyl 3-benzylamino-4-(2,4,5-trifluorophenyl)butanoate (Ib) from (IIa) Through aza-Michael Reaction without Adding of Solvents (Solvent-Free Reaction Conditions)

In a thick-walled glass vial equipped with a magnetic stir bar was placed methyl(E)-4-(2,4,5-trifluorophenyl)-but-2-enoate (IIa) (0.5 mmol, 115 mg) and reaction system was slowly heated to 60° C. under intensive stirring. Afterwards benzylamine (0.6 mmol; 66 mL) was slowly added to (IIa) and such reaction system was vigorously stirred (800 rpm) at 70° C. for 12 hours. The reaction mixture was than extracted with tert-butyl methyl ether (20 mL), organic phase was washed with brine (20 mL) and dried over anhydrous Na$_2$SO$_4$. After evaporation of organic solvent under reduced pressure we obtained crude product (Ib) (85 mg, 50% yield) which was analyzed and confirmed with $^1$H and $^{13}$C NMR.

Example 17

Synthesis of methyl 3-benzylamino-4-(2,4,5-trifluorophenyl)butanoate (Ib) from (IIa) through aza-Michael reaction without adding of solvents in the presence of catalytic amount of DBSA at ambient temperature In a thick-walled glass vial equipped with a magnetic stir bar were placed methyl(E)-4-(2,4,5-trifluorophenyl)-but-2-enoate (IIa) (0.5 mmol, 115 mg), acid catalyst DBSA (0.1 mmol, 32 mg) and such reaction system was vigorously stirred for 15 min at ambient temperature. Afterwards benzylamine (0.6 mmol; 66 mL) was slowly added and reaction mixture was stirred (800 rpm) for 48 hours under ambient temperature. The reaction mixture was than extracted with tert-butyl methyl ether (20 mL), organic phase was washed with aqueous solution of NaHCO$_3$ (20 mL) and dried over anhydrous Na$_2$SO$_4$. After evaporation of organic solvent under reduced pressure we obtained crude product (Ib) (105 mg, 62% yield) which was analyzed and confirmed with $^1$H and $^{13}$C NMR.

Example 18

Synthesis of methyl 3-benzylamino-4-(2,4,5-trifluorophenyl)butanoate (Ib) from (IIa) through aza-Michael reaction without adding of solvents in the presence of phosphotungstic acid In a thick-walled glass vial equipped with a magnetic stir bar was placed methyl(E)-4-(2,4,5-trifluorophenyl)-but-2-enoate (IIa) (0.5 mmol, 115 mg) and after that 12-phosphotungstic acid was added (0.025 mmol, 5 mol % according to (IIa)) and neat reaction mixture was intensively stirred (700 rpm) for 10 min at 60° C. Afterwards benzylamine (0.6 mmol, 66 mL) was slowly dropped and such reaction system was stirred at 60° C. for 18 hours. Reaction mixture was diluted with saturated aqueous solution of NaCl (3.5 mL) and extracted with EtOAc (35 mL). The organic phase was dried over anhydrous Na$_2$SO$_4$ and solvent was evaporated under reduced pressure. The obtained crude product (Ib) (68 mg, 40% yield) was analyzed and confirmed with $^1$H NMR spectroscopy.

Example 19

Synthesis of methyl 3-benzylamino-4-(2,4,5-trifluorophenyl)butanoate (Ib) from (IIa) through aza-Michael reaction without adding of solvents in the presence of sodium dodecysulfate (SDS)

In a thick-walled glass vial equipped with a magnetic stir bar was placed methyl(E)-4-(2,4,5-trifluorophenyl)-but-2-enoate (IIa) (0.5 mmol, 115 mg) and after that anionic surfactant SDS was added (0.1 mmol, 20 mol % according to (IIa)) and neat reaction mixture was intensively stirred (700 rpm) for 20 min at 60° C. Afterwards benzylamine (0.6 mmol, 66 mL) was slowly added (20 min) and such reaction system was stirred at 60° C. for 16 hours. Reaction mixture was diluted with saturated aqueous solution of NaCl (3.5 mL) and gently extracted with EtOAc (35 mL). The organic phase was dried over anhydrous Na$_2$SO$_4$ and solvent was evaporated under reduced pressure. The obtained crude product (Ib) (105 mg, 61% yield) was analyzed and confirmed with $^1$H NMR spectroscopy.

The reaction was successfully performed (55% yield) also at ambient temperature at longer reaction time (48 h).

Example 20

Synthesis of methyl 3-benzylamino-4-(2,4,5-trifluorophenyl)butanoate (Ib) from (IIa) through aza-Michael Reaction without Adding of Solvents in the Presence of Cetyltrimethylammonium Bromide (CTAB)

In a thick-walled glass vial equipped with a magnetic stir bar was placed methyl(E)-4-(2,4,5-trifluorophenyl)-but-2- enoate (IIa) (0.5 mmol, 115 mg) and after that cationic surfactant CTAB was added (0.1 mmol, 20 mol % according to (IIa)) and neat reaction mixture was intensively stirred (700 rpm) for 20 min at 60° C. Afterwards benzylamine (0.6 mmol, 66 mL) was slowly added (20 min) and such reaction system was stirred at 60° C. for 18 hours. Reaction mixture was diluted with saturated aqueous solution of NaCl (3.5 mL) and extracted with EtOAc (35 mL). The organic phase was dried over anhydrous $Na_2SO_4$ and solvent was evaporated under reduced pressure. The obtained crude product (Ib) (98 mg, 57% yield) was analyzed and confirmed with $^1H$ NMR spectroscopy.

The reaction was successfully performed (51% yield) also at ambient temperature at longer reaction time (48 h).

Example 21

Synthesis of methyl 3-(benzyloxyamino)-4-(2,4,5-trifluorophenyl)butanoate (Ie) from (IIa) in the presence of surfactant-type-Brønsted-acid activator 4-dodecybenzenesulfonic acid (DBSA) in water as reaction medium Into a two-necked 250 mL flask equipped with a magnetic stir bar and septums was placed DBSA (30 mol %, 13.80 mmol, 4.60 g) and totally dissolved in deionized water (30-40 mL). Afterwards aqueous solution of O-benzylhydroxylamine hydrochloride (1.2 equiv. according to (IIa), 55.9 mmol, 8.9 g, neutralized beforewith 1.2 equiv. of NaOH) was added in an hour and reaction system was slowly heated to 60° C. Finally starting material methyl(E)-4-(2,4,5-trifluorophenyl)-but-2-enoate (IIa) (46.6 mmol, 10.7 g) was added (slow addition for 5 hours) and such reaction mixture was then vigorously stirred (800 to 1000 rpm) at 80° C. for 24 hours. Reaction mixture was diluted with aqueous solution of 1M NaOH and extracted with n-heptane (3×60 mL). The combined organic phases were washed with 1 M aqueous solution of HCl and after that frequently with water. Organic phase was dried over anhydrous $Na_2SO_4$ and organic solvent was evaporated under reduced pressure. The obtained product (Ie) (13.85 g, 84% yield) was analyzed and confirmed using $^1H$, $^{19}F$ and $^{13}C$ NMR analysis.

$^1H$ NMR (500 MHz, CDCl$_3$, ppm) δ 7.35-7.45 (m, 5ArH), 7.10 (m, 1ArH), 6.90 (m, 1ArH), 5.85 (bs, NH), 4.65 (s, 2H), 3.65 (s, 3H), 3.45-3.55 (m, 1H), 2.90 (ddd, J=14 Hz, J=8.7 Hz, J=1.4 Hz, 1H), 2.75 (ddd, J=14 Hz, J=7.8 Hz, J=1.4 Hz, 1H), 2.50 (dd, J=16 Hz, J=7.8 Hz, 1H), 2.45 (dd, J=16 Hz, J=5.2 Hz, 1H). $^{13}C$ (125 MHz, CDCl$_3$, ppm) δ 30.6, 36.0, 51.6, 57.5, 75.2, 105.4 (m), 119.1 (m), 121.5 (m), 127.3, 128.5, 137.5, 145.7 (m, C—F), 149.7 (m, C—F), 157.0 (m, C—F), 172.2 (CO).

$^{19}F$ NMR (470 MHz, CDCl$_3$, ppm) δ −119.9 (m), −136.9 (m), −143.9 (m).

Example 22

Synthesis of methyl 3-(benzyloxyamino)-4-(2,4,5-trifluorophenyl)butanoate (Ie) from (IIa) in water in the presence of 2,2,2-trifluoroethanol (TFE) as promoter Into a flask equipped with a magnetic stir bar were placed O-benzylhydroxylamine hydrochloride (0.7 mmol, 112 mg), NaOH (0.7 mmol, 28 mg) and deionized water was added. After 15 min TFE (2.5 mmol, 180 mL) was added and such reaction system was heated to 60° C. Afterwards methyl(E)-4-(2,4,5-trifluorophenyl)-but-2-enoate (IIa) (0.5 mmol, 115 mg) was slowly added and final reaction mixture was intensively stirred (900 rpm) at 60° C. for 24 hours. Reaction mixture was diluted with saturated aqueous solution of NaCl (3.5 mL) and extracted with EtOAc (2×25 mL). The combined organic phases were dried over anhydrous $Na_2SO_4$ and organic solvent was evaporated under reduced pressure. The obtained product (Ie) (75 mg, 42% yield) was analyzed and confirmed with $^1H$, $^{19}F$ and $^{13}C$ NMR analysis.

Example 23

Synthesis of methyl 3-(benzyloxyamino)-4-(2,4,5-trifluorophenyl)butanoate (Ie) from (IIa) in water in the presence of SDS and TFE as promoters Into a flask equipped with a magnetic stir bar were placed O-benzylhydroxylamine hydrochloride (0.7 mmol, 112 mg), NaOH (0.7 mmol, 28 mg) and deionized water (2.5 mL). Afterwards catalytic amount of SDS (0.04 mmol, 12 mg) was added and such reaction system was stirred at ambient temperature for 10 minutes. In the next step starting material methyl(E)-4-(2,4,5-trifluorophenyl)-but-2-enoate (IIa) was slowly dropped into the reaction mixture and system was heated to 60° C. Finally the TFE (5 equiv.; 180 µL) was added and such reaction mixture was vigorously stirred (800 rpm) at 60° C. for 15 hours. Reaction mixture was diluted with saturated aqueous solution of NaCl (3.5 mL) and gently extracted with EtOAc (2×30 mL). The combined organic phases were dried over anhydrous $Na_2SO_4$ and organic solvent was evaporated under reduced pressure. The obtained product (Ie) (123 mg, 70.5% yield) was analyzed and confirmed with $^1H$, $^{19}F$ and $^{13}C$ NMR analysis.

Example 24

Synthesis of methyl 3-(benzyloxyamino)-4-(2,4,5-trifluorophenyl)butanoate (Ie) from (IIa) in water in the presence of Sc(OTf)$_3$ and SDS as catalysts Into a flask equipped with a magnetic stir bar were placed O-benzylhydroxylamine hydrochloride (0.7 mmol, 112 mg), NaOH (0.7 mmol, 28 mg) and deionized water (2.5 mL). Afterwards SDS (0.1 mmol; 29 mg; 20 mol % according to (IIa)) and Sc(OTf)$_3$ (0.1 mmol; 49 mg; 20 mol %) and such reaction system was heated to 60° C. Starting material methyl (E)-4-(2,4,5-trifluorophenyl)-but-2-enoate (IIa) (0.5 mmol, 115 mg) was slowly added and final reaction mixture was intensively stirred (900 rpm) at 60° C. for 24 hours. Reaction mixture was diluted with saturated aqueous solution of NaCl (3.5 mL) and gently extracted with EtOAc (2×25 mL). The combined organic phases were dried over anhydrous $Na_2SO_4$ and organic solvent was evaporated under reduced pressure. The obtained product (Ie) (110 mg, 62% yield) was analyzed and confirmed with $^1H$, $^{19}F$ and $^{13}C$ NMR analysis.

Example 25

Synthesis of methyl 3-benzylamino-4-(2,4,5-trifluorophenyl)butanoate (Ib) from (IIa) through aza-Michael reaction in aqueous methanol in the presence of DBSA as catalyst In a thick-walled glass vial equipped with a magnetic stir bar was placed methyl(E)-4-(2,4,5-trifluorophenyl)-but-2-enoate (IIa) (0.5 mmol, 115 mg) which was than vigorously stirred in 2.5 mL of water (900 rpm) to obtain well dispersed aqueous system. Afterwards DBSA (20 mol % according to (IIa)) was added, followed by slow addition of methanol (5 mmol, 10 equiv. according to (IIa)). The reaction system was heated to 60° C. and benzylamine (0.6 mmol, 66 µL) was slowly added and such reaction mixture was vigorously stirred (900 rpm) at 60° C. for 16 hours. Methanol was first evaporated under reduced pressure, organic aqueous residue was extracted with EtOAc (2×35 mL) and combined organic phases were finally washed with brine (1×40 mL) and dried over Na$_2$SO$_4$. After the solvent was evaporated under reduced pressure, the obtained crude product was purified with column chromatography (SiO$_2$, n-hexane:ethylacetate=2:1) to obtain pure (Ib) (98 mg; 58% yield) which was analyzed and determined with $^1$H, $^{13}$C NMR analysis.

Example 26

Synthesis of methyl 3-(benzyloxy-amino)-4-(2,4,5-trifluorophenyl)butanoate (Ie) from (IIa) in methanol in the presence of DBSA as catalyst Into a flask equipped with a magnetic stir bar were placed O-benzylhydroxylamine hydrochloride (0.7 mmol, 112 mg), NaOH (0.7 mmol, 28 mg) and methanol (2.5 mL). During the intensive stirring of the reaction system, DBSA (20 mol % according to (IIa)) was added and such a mixture was heated to 60° C. Afterwards methyl(E)-4-(2,4,5-trifluorophenyl)-but-2-enoate (IIa) was slowly dropped into the reaction mixture and system was stirred at 60° C. for 20 hours. Methanol was first evaporated, residue was extracted with EtOAc (2×30 mL). The combined organic phases were dried over anhydrous Na$_2$SO$_4$ and organic solvent was evaporated under reduced pressure. The obtained product (Ie) (85 mg, 48% yield) was analyzed and confirmed with $^1$H and $^{13}$C NMR analysis.

Example 27

Synthesis of methyl 3-(phenoxy-amino)-4-(2,4,5-trifluorophenyl)butanoate (Im) from (IIa) in the presence of surfactant-type-Brønsted-acid DBSA in water as reaction medium Into a flask equipped with a magnetic stir bar were placed O-phenylhydroxylamine hydrochloride (0.7 mmol, 102 mg), NaOH (0.7 mmol, 28 mg) and deonized water was added. After 15 minutes of stirring, DBSA (0.1 mmol, 33 mg) was added and reaction system was heated to 60° C. under intensive stirring (900 rpm). Afterwards methyl(E)-4-(2,4,5-trifluorophenyl)-but-2-enoate (IIa) (0.5 mmol, 115 mg) was slowly added and such reaction mixture was vigorously stirred at 70° C. for 20 hours. Reaction mixture was diluted with saturated aqueous solution of NaHCO$_3$ (3.5 mL) and extracted with EtOAc (2×30 mL). The combined organic phases were finally washed with brine (1×40 mL), dried over anhydrous Na$_2$SO$_4$ and organic solvent was evaporated under reduced pressure. The obtained product (Im) (68 mg, 40% yield) was analysed and determined with $^1$H NMR analysis.
$^1$H NMR (500 MHz, CDCl$_3$, ppm) δ 7.45 (m, 2ArH), 7.0-7.35 (m, 3ArH), 6.80-6.95 (m, 2ArH), 3.70 (s, 3H), 3.65 (m, 1H), 2.95 (dd, J=6.8 Hz, J=14.5 Hz, 1H), 2.80 (dd, J=7.1 Hz, J=14.5 Hz, 1H), 2.65 (dd, J=8.0 Hz, J=16.5 Hz, 1H), 2.50 (dd, J=4.9 Hz, J=16.5 Hz, 1H), 2.35 (bs, NH).

Example 28

Preparation of optical enriched methyl 3-(benzyloxyamino)-4-(2,4,5-trifluorophenyl)butanoate (Ie) from (IIa) in water as reaction medium in the presence of L-proline as catalyst Into a flask equipped with a magnetic stir bar were placed O-benzylhydroxylamine hydrochloride (1.1 mmol, 176 mg), NaOH (1.1 mmol, 45 mg) and deionized water (5 mL) was added. Afterwards Brønsted acid-surfactant-combined type catalyst DBSA (20 mol %, 0.2 mmol, 65 mg) was added and such reaction mixture was vigorously stirred (900 rpm) for 20 min followed then by addition of amino acid catalyst L-proline (10 mol % according to starting material IIa). Such reaction system was heated between 70 to 80° C. and finally methyl(E)-4-(2,4,5-trifluorophenyl)-but-2-enoate (IIa) (1.0 mmol, 230.0 mg) was slowly dropped. Such reaction mixture was intensively stirred at 80° C. for 20 hours. Reaction mixture was diluted with saturated aqueous solution of NaHCO$_3$ (5 mL) and extracted with EtOAc (2×25 mL). The combined organic phases were finally washed with brine (1×30 mL), dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (190 mg, 54% yield) of pure product (enantiomeric mixture) (Ie). The product was finally analysed and confirmed with $^1$H NMR analysis. HPLC chiral analysis of the enantiomeric mixture showed a weak chiral induction with 20% enantiomeric excess.

Example 29

Preparation of optical enriched methyl 3-(benzyloxyamino)-4-(2,4,5-trifluorophenyl)butanoate (Ie) from (IIa) in water as reaction medium in the presence of L-proline as catalyst and TFE as promoter Into a flask equipped with a magnetic stir bar were placed O-benzylhydroxylamine hydrochloride (1.1 mmol, 176 mg), NaOH (1.1 mmol, 45 mg) and deionized water (5 mL) was added. Afterwards amino acid catalyst L-proline (10 mol % according to starting material IIa) was added followed by slow addition of TFE (5 mmol; 360 µL) and such reaction mixture was vigorously (900 rpm) stirred for 20 min. Finally, methyl(E)-4-(2,4,5-trifluorophenyl)-but-2-enoate (IIa) (1.0 mmol, 230 mg) was slowly dropped and reaction system was intensively stirred (900 rpm) at 80° C. for 24 hours. Reaction mixture was diluted with saturated aqueous solution of NaCl (5 mL) and extracted with EtOAc (2×30 mL). The combined organic phases were dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (200 mg, 57% yield) of pure product (enantiomeric mixture) (Ie). The product was finally analyzed and confirmed with $^1$H NMR analysis. HPLC chiral analysis of the enantiomeric mixture showed a weak chiral induction with 15% enantiomeric excess.

Example 30

Preparation of optical enriched methyl 3-(benzyloxyamino)-4-(2,4,5-trifluorophenyl)butanoate (Ie) from (IIa) in water as reaction medium in the presence of thiourea-based organocatalyst Into a flask equipped with a magnetic stir bar was placed DBSA (20 mol % according to IIa, 0.1 mmol, 33 mg) and totally dissolved in deionized water. Afterwards starting material methyl(E)-4-(2,4,5-trifluorophenyl)-but-2-enoate (IIa) (0.5 mmol, 115 mg) and chiral inductor/catalyst N-[3,5-bis(trifluoromethyl)phenyl]-N'-[6'-methoxy-9-cinchonanyl]thiourea (20 mol %, 0.1 mmol, 60 mg) were added and such reaction mixture was stirred at room temperature for 15 to 20 min. Finally, previously neutralized aqueous solution of O-benzylhydroxylamine hydrochloride (1.3 equiv., 0.65 mmol, 105 mg, neutralized with 1.3 equiv. of NaOH) was slowly dropped into the system and such reaction mixture was vigorously stirred (900 rpm) at 80° C. for 24 hours. Reaction mixture was diluted with saturated aqueous solution of NaHCO$_3$ (5 mL) and extracted with EtOAc (2×30 mL). The combined organic phases were finally washed with brine (2×40 mL), dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (100 mg, 56% yield) of pure product (enantiomeric mixture) (Ie). The product was finally analyzed and confirmed with $^1$H NMR analysis. HPLC chiral analysis of the enantiomeric mixture showed a modest chiral induction with 25% enantiomeric excess.

Example 31

Preparation of optical enriched methyl 3-(benzyloxyamino)-4-(2,4,5-trifluorophenyl)butanoate (Ie) from (IIa) in water as reaction medium in the presence of thiourea-based organocatalyst Into a flask equipped with a magnetic stir bar was placed DBSA (20 mol %, 0.1 mmol, 33.0 mg) and totally dissolved in deionized water. Afterwards starting material methyl(E)-4-(2,4,5-trifluorophenyl)-but-2-enoate (IIa) (0.5 mmol, 115 mg) and chiral inductor/catalyst 2-[[3,5-bis(trifluoromethyl)phenyl]thioureido]-N-benzyl-N,3,3-trimethylbutanamide (20 mol %, 0.1 mmol, 51 mg) were added and such reaction mixture was stirred at room temperature for 20 min. Finally, previously neutralized aqueous solution of O-benzylhydroxylamine hydrochloride (1.5 equiv., 0.75 mmol, 105 mg, neutralized using 1.5 equiv. of NaOH) was slowly dropped into the system and such reaction mixture was vigorously stirred (900 rpm) at 80° C. for 24 hours. Reaction mixture was diluted with saturated aqueous solution of NaHCO$_3$ (5 mL) and extracted with CH$_2$Cl$_2$ (2×30 mL). The combined organic phases were finally washed with brine (1×40 mL), dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (125 mg, 71% yield) of pure product (enantiomeric mixture) (Ie). The product was finally analyzed and confirmed with $^1$H NMR analysis. HPLC chiral analysis of the enantiomeric mixture showed a chiral induction with 38% enantiomeric excess.

Example 32

Preparation of optical enriched methyl 3-(benzyloxyamino)-4-(2,4,5-trifluorophenyl)butanoate (Ie) from (IIa) in water as reaction medium in the presence of cinchona alkaloids as catalysts Into a flask equipped with an magnetic stir bar was placed aqueous solution of DBSA followed by addition of starting material methyl(E)-4-(2,4,5-trifluorophenyl)-but-2-enoate (IIa) (0.5 mmol, 115.0 mg), catalyst quinidine (20 mol %, 0.1 mmol, 33 mg) and catalyst activator benzoic acid (40 mol %, 0.2 mmol, 25 mg). Such reaction system was stirred for 30 min at ambient temperature. Afterwards aqueous solution of O-benzylhydroxylamine hydrochloride (1.5 equiv., 0.75 mmol, 105 mg, neutralized using 1.5 equiv. of NaOH) was slowly dropped into reaction system during the heating to 80° C. and such reaction mixture was vigorously stirred (900 rpm) at set temperature for 24 hours. Reaction mixture was diluted with saturated aqueous solution of NaHCO$_3$ (5 mL) and extracted with CH$_2$Cl$_2$ (2×35 mL). The combined organic phases were finally washed with brine (1×40 mL), dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (120 mg, 68% yield) of pure product (enantiomeric mixture) (Ie). The product was finally analyzed and confirmed with $^1$H NMR analysis. HPLC chiral analysis of the enantiomeric mixture showed a weak chiral induction with 15% enantiomeric excess.

Example 33

Preparation of optical enriched methyl 3-(benzyloxyamino)-4-(2,4,5-trifluorophenyl)butanoate (Ie) from (IIa) in water as reaction medium in the presence of cinchona alkaloids Into a flask equipped with an magnetic stir bar was placed aqueous solution of DBSA followed by addition of starting material methyl(E)-4-(2,4,5-trifluorophenyl)-but-2-enoate (IIa) (0.5 mmol, 115 mg), catalyst 6'-methoxycinchonan-9-amine trihydrochloride (20 mol %, 0.1 mmol, 43 mg, neutralized with 0.1 mmol of NaOH) and catalyst activator benzoic acid (50 mol %, 0.25 mmol, 30 mg). Such reaction system was stirred for 30 min at ambient temperature. Afterwards aqueous solution of O-benzylhydroxylamine hydrochloride (1.3 equiv., 0.65 mmol, 105 mg, neutralized using 1.3 equiv. of NaOH) was slowly dropped into reaction system during the heating to 80° C. and such reaction mixture was vigorously stirred (900 rpm) at set temperature for 24 hours. Reaction mixture was diluted with saturated aqueous solution of NaHCO$_3$ (5 mL) and extracted with CH$_2$Cl$_2$ (2×30 mL). The combined organic phases were finally washed with brine (1×40 mL), dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (90 mg, 51% yield) of pure product (enantiomeric mixture) (Ie). The product was finally analyzed and confirmed with $^1$H NMR analysis. HPLC chiral analysis of the enantiomeric mixture showed a weak chiral induction with 22% enantiomeric excess.

Example 34

Preparation of optical enriched methyl 3-(benzyloxyamino)-4-(2,4,5-trifluorophenyl)butanoate (Ie) from (IIa) in water as reaction medium in the presence of imidazolidinone-type organocatalysts Into a flask equipped with a magnetic stir bar was placed DBSA (20 mol %, 0.1 mmol, 33 mg) and totally dissolved in deionized water. Afterwards starting material methyl(E)-4-(2,4,5-trifluorophenyl)-but-2-enoate (IIa) (0.5 mmol, 115 mg) and chiral inductor 2,2,3-trimethyl-5-benzyl-4-imidazolidinone monohydrochloride (20 mol %, 0.1 mmol, 25.5 mg, neutralized with NaOH) were added. Such reaction mixture was stirred at room temperature for 20 min. Finally, previously neutralized aqueous solution of O-benzylhydroxylamine hydrochloride (1.35 equiv., 0.68 mmol, 110 mg, neutralized using 1.35 equiv. of NaOH) was slowly dropped into reaction system and reaction mixture was vigorously stirred (900 rpm) at 80° C. for 20 hours. Reaction mixture was diluted with saturated aqueous solution of NaHCO$_3$ (5 mL)

and extracted with EtOAc (2×30 mL). The combined organic phases were finally washed with brine (1×40 mL), dried over anhydrous Na$_2$SO$_4$ and organic solvent was evaporated under reduced pressure. The obtained crude product (Ie) was purified with column chromatography (SiO$_2$, n-hexane:ethylacetate=2:1 gradient elution) to obtain (95 mg, 54% yield) of pure product (enantiomeric mixture) (Ie). The product was finally analyzed and confirmed with $^1$H NMR analysis. HPLC chiral analysis of the enantiomeric mixture showed a weak chiral induction with 18% enantiomeric excess.

LIST OF REFERENCES

WO 03/004498
WO 09/06447
WO 04/085378
WO 05/097733
WO 06/081151
WO 04/085661
WO 04/087650
US 2009/0192326
US 2006/0052382
WO 09/045507
WO 09/045507
WO 2010/122578
Hansen, K. B.; et. al. *J. Am. Chem. Soc.* 2009, 131, 8798-8804.
Hansen K. B.; et. al. *Org. Process Res. Dev.* 2005, 9, 634-639.
Hsiao, Y.; et. al. *J. Am. Chem. Soc.*, 2004, 126, 9918-9919.
Kubryl, M.; et. al. *Tetrahedron Asymmetry* 2006, 17, 205-209.
Liu, F.; et. al. *J. Chem. Res.* 2010, 34, 230-232.
Savile, C. K.; et. al. *Science* 2010, 329, 305-309.
Desai, A.; et. al. *Angew. Chem. Int. Ed.* 2011, 50, 2-5.
Mutti, F. G.; et. al. *ChemCatChem* 2011, 3, 109-111.

The following pages of the description refer to the embodiments of the invention listed as separate items:
1. A process for the preparation of an intermediate of formula I,

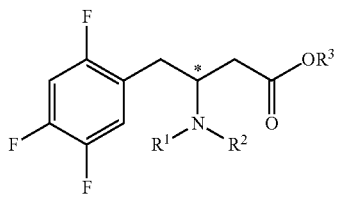

wherein the stereogenic center marked with an * is either in (R)- or (S)-configuration at marked center, or it is in racemic form, and
wherein R$^1$ and R$^2$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted;
(ix) alkoxycarbonyl residues optionally chiral, having from 2 to 13 carbon atoms;
(x) aryloxycarbonyl residues optionally chiral, having from 7 to 25 carbon atoms;
(xi) tosyl;
(xii) silyl residues optionally chiral, having from 3 to 15 carbon atoms; and
(xiii) silyloxy residues optionally chiral, having from 3 to 15 carbon atoms;
wherein R$^3$ is selected from alkyl residues having from 1 to 6 carbon atoms;
the process comprising the steps of:
(a) providing an intermediate of formula II,

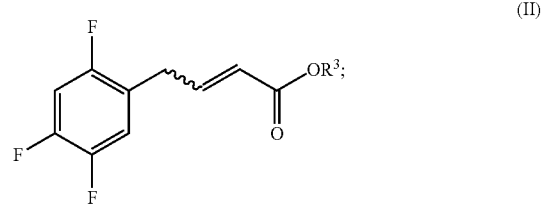

(b) reacting the intermediate of formula II with an amine of formula III

wherein R$^1$ and R$^2$ are as defined above, in a protic solvent, particularly in water; or in a mixture of protic solvents, wherein the mixture particularly comprises water; or without adding of solvents in step (b); to obtain an intermediate of formula I.
2. The process of item 1, wherein in step (b) the solvent is selected from water, methanol, ethanol, iso-propanol, tert-butanol, trifluoroethanol, hexafluoro-2-propanol, amyl alcohol and any combination thereof, and is particularly water.
3. The process of item 1, wherein step (b) is carried out without adding solvents.
4. The process of items 1 to 3, wherein step (b) is carried out at a temperature of 20° C. to 100° C., preferably of 20° C. to 85° C.
5. The process of any of items 1 to 4, wherein R$^1$ and R$^2$ are identical, and are selected from
(i) hydrogen;
(ii) alkyl residues optionally chiral, having from 1 to 12 carbon atoms, wherein the alkyl residues are optionally aryl and/or aryloxy substituted;
(iii) aryl residues optionally chiral, having from 6 to 24 carbon atoms, wherein the aryl residues are optionally alkyl and/or alkyloxy substituted;
(iv) benzyl;
(v) alkoxycarbonyl residues optionally chiral, having from 2 to 13 carbon atoms;
(vi) aryloxycarbonyl residues optionally chiral, having from 7 to 25 carbon atoms;
(vii) silyl residues optionally chiral, having from 3 to 15 carbon atoms;

and are particularly hydrogen, methyl, N-α-methylbenzyl, or trimethylsilyl.

6. The process of any of items 1 to 4, wherein $R^1$ and $R^2$ are different, and are independently selected from
   (i) hydrogen;
   (ii) alkyl residues optionally chiral, having from 1 to 12 carbon atoms, wherein the alkyl residues are optionally aryl and/or aryloxy substituted;
   (iii) alkyloxy residues optionally chiral, having from 1 to 12 carbon atoms, wherein the alkyloxy residues are optionally aryl substituted;
   (iv) aryl residues optionally chiral, having from 6 to 24 carbon atoms, wherein the aryl residues are optionally alkyl and/or alkyloxy substituted;
   (v) aryloxy residues optionally chiral, having from 6 to 24 carbon atoms, wherein the aryloxy residues are optionally alkyl substituted;
   (vi) benzyl;
   (vii) alkaloyl residues optionally chiral, having from 2 to 13 carbon atoms, wherein the alkaloyl residues are optionally aryl substituted;
   (viii) aroyl residues optionally chiral, having from 7 to 25 carbon atoms, wherein the aryloxy residues are optionally alkyl substituted;
   (ix) alkoxycarbonyl residues optionally chiral, having from 2 to 13 carbon atoms;
   (x) aryloxycarbonyl residues optionally chiral, having from 7 to 25 carbon atoms;
   (xi) tosyl;
   (xii) silyl residues optionally chiral, having from 3 to 15 carbon atoms; and
   (xiii) silyloxy residues optionally chiral, having from 3 to 15 carbon atoms;
   and particularly $R^1$ is hydrogen and $R^2$ is tosyl, $R^1$ is hydrogen and $R^2$ is benzyl, $R^1$ is hydrogen and $R^2$ is N-α-methylbenzyl, $R^1$ is benzyl and $R^2$ is N-α-methylbenzyl, $R^1$ is benzyl and $R^2$ is N-benzyl-1-phenethyl, $R^1$ is hydrogen and $R^2$ is O-benzyl, $R^1$ is hydrogen and $R^2$ is O-methyl, $R^1$ is hydrogen and $R^2$ is tert-butyl-oxy-carbonyl or benzyl-oxy-carbonyl, $R^1$ is hydrogen and $R^2$ is methoxy-phenyl, $R^1$ is hydrogen and $R^2$ is O-phenyl, or $R^1$ is hydrogen and $R^2$ is O-trimethylsilyl.

7. The process of any of the preceding items, wherein the chiral aryl residues are selected from N-α-methylbenzyl, N-Bis[a-methylbenzyl], N-α-ethyl-naphthyl, 2-methoxy-benzyl-1-phenylethyl, 3,4-dimethoxybenzyl-1-phenylethyl, and N-benzyl-1-phenethyl.

8. The process of any of the preceding items, wherein $R^3$ is selected from methyl, ethyl, propyl, cyclopropyl, butyl, pentyl, hexyl, isopropyl, isopentyl, and tert-butyl, and is particularly methyl.

9. The process of any of items 1 to 4, wherein the intermediate of formula I is

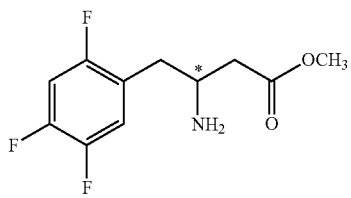
(Ia)

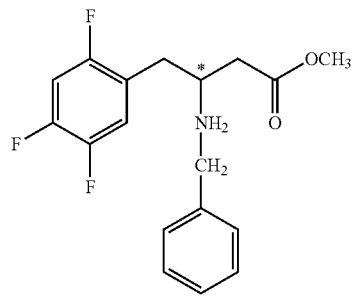
(Ib)

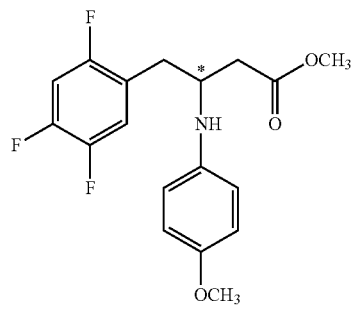
(Ic)

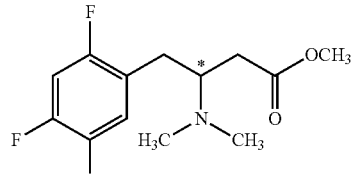
(Id)

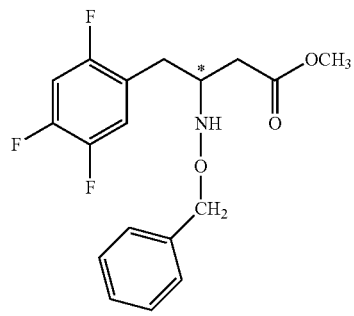
(Ie)

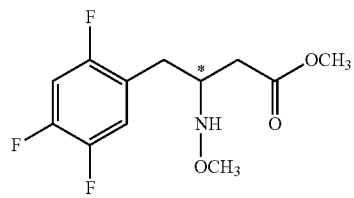
(If)

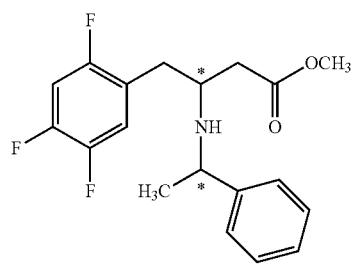
(Ig)

-continued

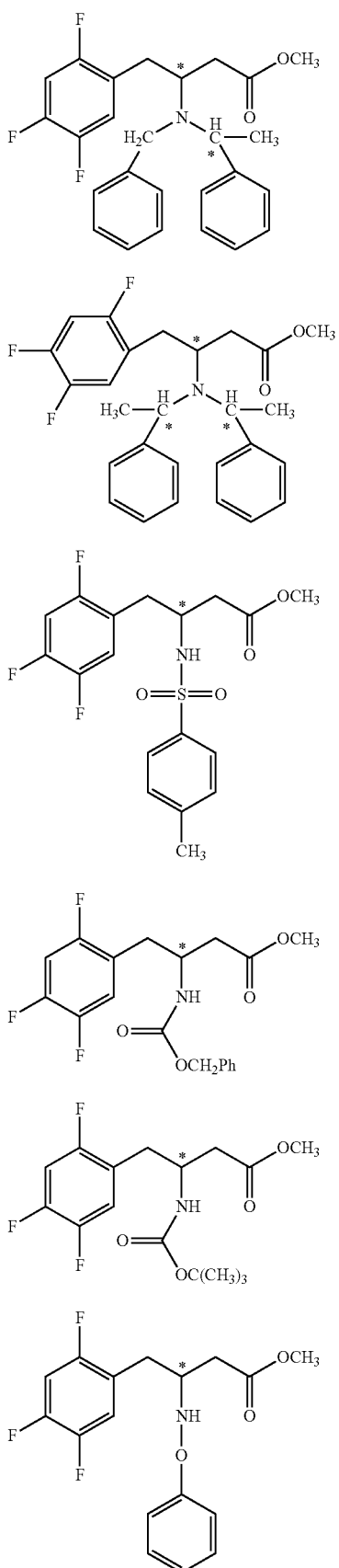

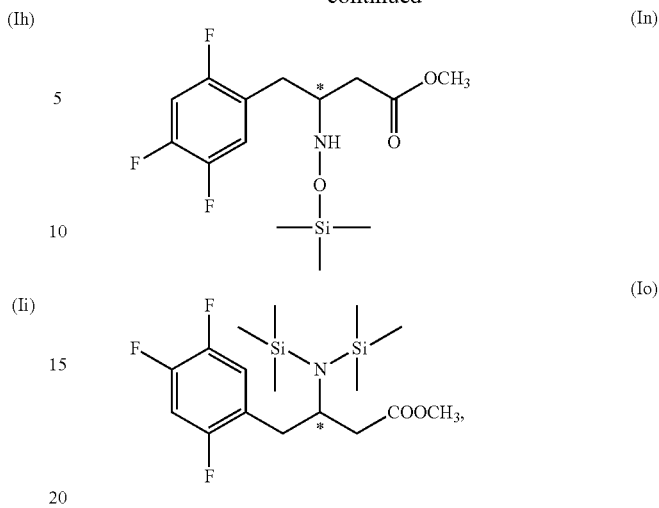

wherein the stereogenic center marked with an * is either in (R)- or (S)-configuration at marked center, or it is in racemic form.

10. The process of any of the preceding items, wherein the amine of formula III is selected from ammonia, an alkyl amine, an aryl amine, an alkyl-aryl amine, a silyl amine, and a silyloxy amine.

11. The process of any of the preceding items, wherein the amine is an alkyl amine and is selected from dimethylamine, tert-butyl-carbamate and O-methylhydroxylamine.

12. The process of any of items 1 to 10, wherein the amine is an aryl amine and is selected from benzylamine, p-methoxybenzylamine, 3,4-dimethoxybenzylamine, p-methoxyaniline, tosylamine, benzyl carbamate dibenzylamine, naphythylamine, O-benzylhydroxylamine, O-phenylhydroxylamine and benzhydrylamine.

13. The process of any of items 1 to 10, wherein the amine is an alkyl-aryl amine and is selected from methyl-phenylamine, N-α-methylbenzylamine, N-bis-[α-methylbenzylamine], and N-benzyl-1-phenylethyl.

14. The process of any of items 1 to 10, wherein the amine is a silyl amine and is selected from hexamethyldisilazane, potassium bis(trimethylsilyl)amide, sodium bis(trimethylsilyl)amide, lithium bis(trimethylsilyl)amide, 1,1,3,3-tetramethyldisilazane and 1,1,3,3-tetramethyl-1,3-diphenylsilazane.

15. The process of any of items 1 to 10, wherein the amine is a silyloxy amine and is selected from O-(trimethylsilyl)hydroxylamine, N,O-bis(trimethylsilyl)hydroxylamine.

16. The process of any of the preceding items, wherein the amine in step (b) is present in an amount of 1.1 to 2.0 equivalents, particularly 1.2 to 1.7 equivalents, with respect to the intermediate of formula H.

17. The process of any of the preceding items, wherein the reaction time is between 5 to 52 hours, particularly between 6 to 48 hours.

18. The process of any of the preceding items, wherein step (b) is a non-catalyzed process.

19. The process of item 18, wherein step (b) is carried out in a protic solvent or in a mixture of protic solvents, and at a temperature of 50° C. to 90° C., preferably of 60° C. to 85° C., and more preferably about 60° C.

20. The process of item 18 or 19, wherein step (b) is carried out in a protic solvent or in a mixture of protic solvents, and the reaction time is between 10 to 30 hours, preferably about 16 hours.

21. The process of item 18, wherein step (b) is carried out without adding of solvents, and at a temperature of 25° C. to 90° C., preferably of 60° C. to 85° C., and more preferably about 70° C.

22. The process of item 18 or 21, wherein step (b) is carried out without adding solvents, and the reaction time is between 8 to 20 hours, preferably about 12 hours.

23. The process of any of items 1 to 17, wherein step (b) is a transition metal catalyzed process, particularly a transition metal catalyzed process using a catalyst comprising a transition metal compound, and optionally at least one ligand.

24. The process of item 23, wherein in step (b) the transition metal compound is selected from copper compounds, indium compounds, zinc compounds, iron compounds, manganese compounds, cerium compounds, bismuth compounds, scandium compounds, ytterbium compounds, yttrium compounds, tin compounds and vanadium compounds, particularly selected from copper compounds, indium compounds, scandium compounds, ytterbium compounds, and iron compounds.

25. The process of item 23 or 24, wherein in step (b) the transition metal compound is a copper compound and is selected from copper(I) acetate, copper(I) chloride, copper (II) chloride, cooper(I) triflate, copper(II) triflate, cooper (II) acetylacetonate, cooper(II) chlorate, and any combination thereof, and is particularly selected from copper(I) acetate, copper(II) triflate, and copper(II) bromide.

26. The process of item 23 or 24, wherein in step (b) the transition metal compound is an indium compound and is selected from indium(III) chloride, indium(II) chloride, indium(III) bromide, indium(III) perchlorate, and indium (III) nitrate, and is particularly indium(III) chloride.

27. The process of item 23 or 24, wherein in step (b) the transition metal compound is a scandium compound and is selected from scandium(III) triflate, scandium(III) perchlorate, scandium(III) chloride, and scandium(III) oxalate, and is particularly scandium(III) triflate.

28. The process of item 23 or 24, wherein in step (b) the transition metal compound is an iron compound and is selected from iron(II) chloride, iron(III) chloride, iron(II) acetylacetonate, iron(III) acetylacetonate, iron(III) chloride hexahydrate, iron(III) triflate, iron(III) chlorate, and iron(III) bromide, and is particularly iron(III) chloride.

29. The process of item 23 or 24, wherein in step (b) the transition metal compound is a vanadium compound and is selected from vanadium(III) acetylacetonate, vanadium (V) oxychloride, vanadium(IV) chloride, and particularly vanadium(IV) chloride or oxychloride, and is particularly vanadium(III) acetylacetonate.

30. The process of any of items 23 to 29, wherein in step (b) the transition metal compound is present in an amount of 2-25 mol %, particularly of 4-20 mol %, and more particularly about 8-15 mol % to the intermediate of formula II.

31. The process of any of items 23 to 30, wherein in step (b) the optionally at least one ligand is selected from monophosphine ligands, diphosphine ligands, and any combination thereof.

32. The process of any of items 23 to 31, wherein in step (b) the optionally at least one ligand is selected from monophosphine ligands, and is particularly triphenylphosphine, tributylphosphine, trimethylphosphine, tricyclohexylphosphine, tri-(o-tolyl)phosphine, tri-(2-furyl)phosphine, tris(dimethylamino)phosphine, tribenzylphosphine, tripyrolydinophosphine, tris(4-methoxyphenyl)phosphine, and any combination thereof.

33. The process of any of items 23 to 32, wherein in step (b) the optionally at least one ligand is selected from diphosphine ligands, and is particularly 1,2-bis(diphenyl-phosphino)benzene, 1,1,-bis(di-tert-butylphosphino)ferrocene, (oxydi-2,1-phenylene)bis-(diphenylphosphine), (R)-2,2-bis(diphenylphosphino)-1,1-binaphthalene, (S)-2,2-bis (diphenylphosphino)-1,1-binaphthale, (S,R)-(diphenylphosphino)-ferrocenyl-ethyldi-tert-butylphosphine, (R,S)-(diphenylphosphino)-ferrocenyl-ethyldi-tert-butylphosphine, and any combination thereof.

34. The process of any of items 23 to 33, wherein in step (b) the optionally at least one ligand is present in an amount of 2-20 mol %, particularly of 4-15 mol %, and more particularly 8-10 mol %, with respect to the intermediate of formula II.

35. The process of any of items 23 to 34, wherein the transition metal catalyzed process is optionally carried out in the presence of a base, particularly wherein the base is selected from NatOBu, KOtBu, $K_2CO_3$, $Na_2CO_3$, KOAc, NaOAc, and any combination thereof, more particularly NaOtBu.

36. The process of item 35, wherein the base is present in an amount of 5-25 mol %, particularly of 10-20 mol %, and more particularly about 15 mol %, with respect to the intermediate of formula II.

37. The process of any of items 23 to 34, wherein the transition metal catalyzed process is carried out in the absence of a base.

38. The process of any of items 23 to 37, wherein step (b) is carried out in the presence of a surfactant as defined in any of items 63 to 65.

39. The process of any of items 1 to 17, wherein step (b) is an acid catalyzed process.

40. The process of item 39, wherein in step (b) the acid is a Lewis acid, particularly selected from copper(II) acetate, copper(II) chloride, copper(II) triflate, iron(III) chloride, indium(III) chloride, zinc(II) chloride, scandium(III) triflate, ytterbium(III) triflate, and vanadium(III) acetylacetonate.

41. The process of item 39, wherein in step (b) the acid is a Brønsted acid, particularly selected from 4-dodecylbenzenesulfonic acid (DBSA), phosphotungstic acid, Nafion-H, trifluoromethanesulfonic acid (HOTf), phosphomolybdic acid, methanesulfonic acid, p-toluenesulfonic acid (PTSA), chlorsulfonic acid 2,5-dinitrobenzenesulfonic acid (DNBSA), sulfuric acid, polystyrenesulfonic acid (PSSA), boric acid, phenyboric acid, and any combination thereof, and is particularly DBSA, PSSA or phosphotungstic acid.

42. The process of any of items 39 to 41, wherein step (b) is carried out in a protic solvent or in a mixture of protic solvents, and in step (b) the acid is present in an amount of 5-30 mol %, particularly of 8-25 mol %, and more particularly about 10-20 mol %, to the intermediate of formula II.

43. The process of any of items 39 to 42, wherein step (b) is carried out in a protic solvent or in a mixture of protic solvents, and step (b) is carried out at a temperature of 25° C. to 90° C., preferably of 60° C. to 85° C., and more preferably about 60° C. to 65° C.

44. The process of any of items 39 to 43, wherein step (b) is carried out in a protic solvent or in a mixture of protic solvents, and the reaction time is between 6 to 24 hours, particularly between 10 to 24 hours.

45. The process of any of items 39 to 41, wherein step (b) is carried out without adding of solvents and in step (b) the acid is present in an amount of 3-30 mol %, particularly of 4-25 mol %, and more particularly about 5-20 mol %, to the intermediate of formula H.

46. The process of any of items 39 to 41 and 45, wherein step (b) is carried out without adding of solvents, and step (b) is carried out at a temperature of 20° C. to 90° C., preferably of 20° C. to 60° C.

47. The process of any of items 39 to 41, 45 and 46, wherein step (b) is carried out without adding solvents, and the reaction time is between 10 to 52 hours, particularly between 12 to 48 hours.

48. The process of any of items 1 to 17, and step (b) is an organocatalyzed process, particularly an organocatalyzed process using an optionally chiral organocatalyst.

49. The process of item 48, wherein in step (b) the organocatalyst is selected from amino acid chiral compounds, particularly selected from pyroglutamic acid, threonine, aspartic acid, and any combination thereof.

50. The process of item 48, wherein in step (b) the organocatalyst is selected from proline derivatives.

51. The process of item 48, wherein in step (b) the organocatalyst is selected from imidazolidinone derivatives.

52. The process of item 48, wherein in step (b) the organocatalyst is selected from cinchona alkaloids.

53. The process of item 48, wherein in step (b) the organocatalyst is selected from; tiourea derivatives.

54. The process of any of items 48 to 53, wherein in step (b) the organocatalyst is present in an amount of 1-30 mol %, particularly of 3-25 mol %, and more particularly 6-20 mol %, to the intermediate of formula II.

55. The process of any of items 48 to 54, wherein step (b) is carried out at a temperature of 25° C. to 90° C., preferably of 60° C. to 85° C., and more preferably 60° C. to 80° C.

56. The process of any of items 48 to 55, wherein the reaction time is between 12 to 24 hours, particularly between 15 to 20 hours.

57. The process of any of items 1 to 17, wherein the step (b) is carried out in the presence of a promoter.

58. The process of item 57, wherein in step (b) the promoter is selected from fluorinated alcohols, in particular selected from trifluoroethanol, hexafluoro-2-propanol, and any combination thereof.

59. The process of item 57 or 58, wherein in step (b) the promoter is present in an amount of 1-15 equivalents, particularly of 3-12 equivalents, and more particularly 5-10 equivalents, to the intermediate of formula II.

60. The process of any of items 57 to 59, wherein step (b) is carried out at a temperature of 50° C. to 90° C., preferably of 60° C. to 85° C., and more preferably 60° C. to 80° C.

61. The process of any of items 57 to 60, wherein the reaction time is between 12 to 30 hours, particularly between 15 to 24 hours.

62. The process of any of the items 1 to 17, wherein step (b) is carried out in the presence of a surfactant.

63. The process of item 62, wherein the surfactant is selected from ionic, nonionic surfactants, and the combination thereof.

64. The process of item 62 or 63, wherein the surfactant is an ionic surfactant and is selected from sodium dodecyl sulfate, sodium stearate, sodium N-lauroylsarcosinate, cetyltrimethylammonium bromide, cetyltrimethylammonium chloride, benzyldodecyammonium bromide, and any combination thereof, and is particularly sodium dodecyl sulfate or cetyltrimethylammonium bromide.

65. The process of item 62 or 63, wherein the surfactant is a nonionic surfactant and is selected from D-α-tocopherol polyethylene glycol succinate, 4-octylphenol polyethoxylate, polyoxyethylene sorbitan monolaurate, polyethylene glycol dodecyl ether, and polyoxyethanyl-α-tocopheryl sebacate, and any combination thereof, and is particularly D-α-tocopherol polyethylene glycol succinate or polyoxyethanyl-α-tocopheryl sebacate.

66. The process of any of items 62 to 65, wherein step (b) is carried out in a protic solvent or in a mixture of protic solvents, and the surfactant is present in an amount of 0.5-30 wt %, particularly of 1-20 wt %, and more particularly 2-15 wt %, with respect to the intermediate of formula II.

67. The process of any of items 62 to 66, wherein step (b) is carried out in a protic solvent or in a mixture of protic solvents, and is carried out at a temperature of 25° C. to 90° C., preferably of 60° C. to 85° C., and more preferably 60° C. to 65° C.

68. The process of any of items 62 to 67, wherein step (b) is carried out in a protic solvent or in a mixture of protic solvents, and the reaction time is between 10 to 20 hours, more particularly between 15 to 20 hours.

69. The process of any of items 62 to 65, wherein step (b) is carried out without adding of solvents, and the surfactant is present in an amount of 5-40 wt %, particularly of 10-30 wt %, and more particularly 15-20 wt %, with respect to the intermediate of formula II.

70. The process of any of items 62 to 65 and 69, wherein step (b) is carried out without adding of solvents, and is carried out at a temperature of 25° C. to 90° C., preferably of 60° C. to 85° C., and more preferably 60° C. to 65° C.

71. The process of any of items 62 to 65, 69 and 70, wherein step (b) is carried out without adding of solvents, and the reaction time is between 10 to 20 hours, more particularly between 16 to 18 hours.

72. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

(II)

(b) reacting the intermediate of formula II with benzylamine present in an amount of 1.1 to 1.5 equivalents, preferably about 1.2 equivalents, with respect to the intermediate of formula II, in water at 20° C. to 65° C., preferably at 60° C., for 10 to 30 hours, preferably 24 hours, to obtain an intermediate of formula I.

73. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

(II)

(b) reacting the intermediate of formula II with benzylamine present in an amount of 1.1 to 1.5 equivalents, preferably about 1.2 equivalents, with respect to the intermediate of formula II, in water at 30° C. for 5 to 7 hours, preferably 6 hours, in the presence of
(i) copper(II) acetate, preferably present in an amount of 4-12 mol %, more preferably about 10 mol %, with respect to the intermediate of formula II;
(ii) triphenylphosphine, preferably present in an amount of 4-12 mol %, more preferably 8-10 mol %, with respect to the intermediate of formula II,
(iii) sodium dodecylsulfate, preferably present in an amount of 4-20 mol %, more preferably 8-10 mol %, with respect to the intermediate of formula II, and
(iv) NatOBu, preferably present in an amount of 10-20 mol %, more preferably about 15 mol %, with respect to the intermediate of formula II, to obtain an intermediate of formula I.

74. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

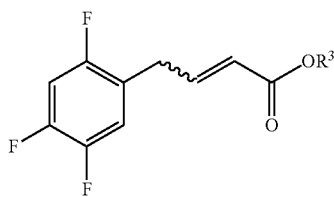

(II)

(b) reacting the intermediate of formula II with benzylamine present in an amount of 1.1 to 1.5 equivalents, preferably about 1.2 equivalents, with respect to the intermediate of formula II, in water at 30° C. to 65° C., preferably at 60° C., for 5 to 7 hours, preferably 6 hours,
in the presence of
(i) copper(II) acetate, preferably present in an amount of 4-12 mol %, more preferably about 10 mol %, with respect to the intermediate of formula II;
(ii) sodium dodecylsulfate, preferably present in an amount of 4-20 mol %, more preferably 8-10 mol %, with respect to the intermediate of formula II, and to obtain an intermediate of formula I.

75. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

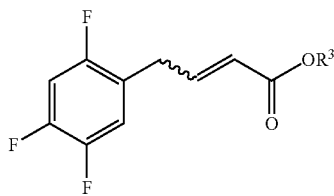

(II)

(b) reacting the intermediate of formula II with benzylamine present in an amount of 1.1 to 1.5 equivalents, preferably about 1.2 equivalents, with respect to the intermediate of formula II, in water at 50° C. to 95° C., preferably at 80° C., for 10 to 20 hours, preferably 15 hours, in the presence of
(i) copper(II) bromide, preferably present in an amount of 10-20 mol %, more preferably about 15 mol %, with respect to the intermediate of formula II; or
(ii) iron(III) chloride, preferably present in an amount of 10-20 mol %, more preferably about 15 mol %, with respect to the intermediate of formula II;

to obtain an intermediate of formula I.

76. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

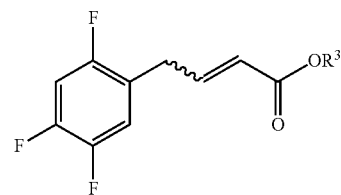

(II)

(b) reacting the intermediate of formula II with benzylamine present in an amount of 1.1 to 1.5 equivalents, preferably about 1.2 equivalents, with respect to the intermediate of formula II, in water at 25° C. to 90° C., preferably at 60° C., for 15 to 25 hours, preferably 20 hours,
in the presence of
(i) indium(III) chloride, preferably present in an amount of 10-20 mol %, more preferably about 15 mol %, with respect to the intermediate of formula II;

to obtain an intermediate of formula I.

77. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

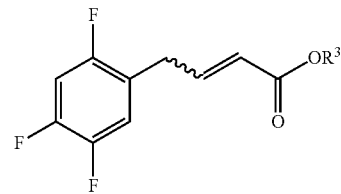

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 80° C., for 10 to 20 hours, preferably 16 hours,
in the presence of
(i) 2,2,2-trifluoroethanol, preferably present in an amount of 5-15 equivalents, more preferably about 5-10 equivalents, with respect to the intermediate of formula II;

to obtain an intermediate of formula I.

78. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

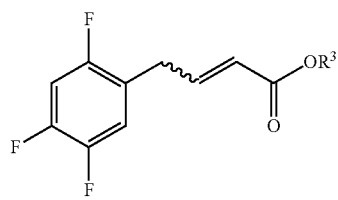

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 15 to 25 hours, preferably 20 hours,
in the presence of
(i) 1,1,1,3,3,3-hexafluoro-2-propanol, preferably present in an amount of 5-15 equivalents, more preferably about 5-10 equivalents, with respect to the intermediate of formula II;
to obtain an intermediate of formula I.

79. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

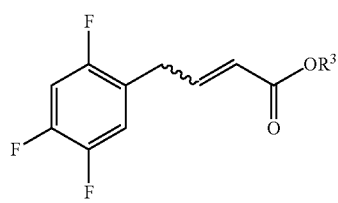

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 20 hours, preferably 15 hours,
in the presence of
(i) D-α-tocopherol-polyethyleneglycol-succinate, preferably present in an amount of 2-15 wt % with respect to the intermediate of formula II; or
(ii) polyoxyethanyl-α-tocopheryl-sebacate, preferably present in an amount of 2-15 wt % with respect to the intermediate of formula II;
to obtain an intermediate of formula I.

80. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

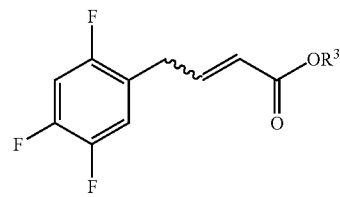

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 60° C., for 15 to 25 hours, preferably 20 hours,
in the presence of
(i) sodium dodecylsulfate, preferably present in an amount of 2-15 wt % with respect to the intermediate of formula II;
to obtain an intermediate of formula I.

81. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

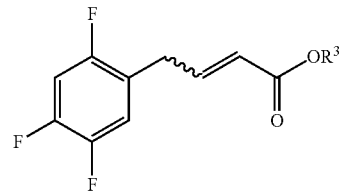

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 5 to 20 hours, preferably 12 hours,
in the presence of
(i) 4-dodecybenzenesulfonic acid (DBSA), preferably present in an amount of 15-25 mol %, more preferably about 20 mol %, with respect to the intermediate of formula II;
to obtain an intermediate of formula I.

82. The process of item 1, wherein $R^1$ is hydrogen, $R^2$ is benzyl and $R^3$ is methyl;
the process comprises or consists the steps of:
(a) providing an intermediate of formula II, wherein $R^3$ is methyl;

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 15 hours, preferably 20 hours, in the presence of (i) polystyrenesulfonic acid (PSSA), preferably present in an amount of 5-15 mol %, more preferably about 10 mol %, with respect to the intermediate of formula II;

to obtain an intermediate of formula I.

83. The process of item 1, wherein $R^1$ is hydrogen, $R^2$ is benzyl and $R^3$ is methyl;

the process comprises or consists the steps of:

(a) providing an intermediate of formula II, wherein $R^3$ is methyl;

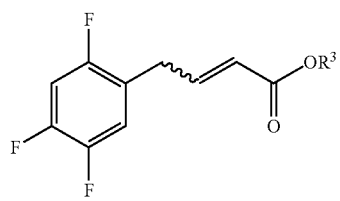

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 25 hours, preferably 15 hours, in the presence of (i) phosphotungstic acid, preferably present in an amount of 5-15 mol %, more preferably about 10 mol %, with respect to the intermediate of formula II;

to obtain an intermediate of formula I.

84. The process of item 1, wherein $R^1$ is hydrogen, $R^2$ is benzyl and $R^3$ is methyl;

the process comprises or consists the steps of:

(a) providing an intermediate of formula H, wherein $R^3$ is methyl;

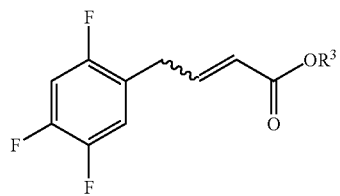

(II)

(b) reacting the intermediate of formula II with benzylamine present in an amount of 1.1 to 1.5 equivalents, preferably about 1.2 equivalents, with respect to the intermediate of formula II, in water at 50° C. to 90° C., preferably at 65° C., for 10 to 25 hours, preferably 18 hours, in the presence of (i) acid activator Nafion NR50, preferably present in an amount of 5-15 mol %, more preferably about 10 mol %, with respect to the intermediate of formula II;

to obtain an intermediate of formula I.

85. The process of item 1, wherein $R^1$ is hydrogen, $R^2$ is benzyl and $R^3$ is methyl;

the process comprises or consists the steps of:

(a) providing an intermediate of formula II, wherein $R^3$ is methyl;

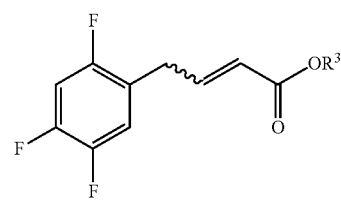

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 70° C., for 8 to 20 hours, preferably 12 hours, to obtain an intermediate of formula I.

86. The process of item 1, wherein $R^1$ is hydrogen, $R^2$ is benzyl and $R^3$ is methyl;

the process comprises or consists the steps of:

(a) providing an intermediate of formula II, wherein $R^3$ is methyl;

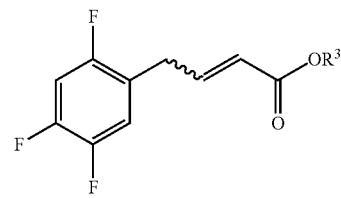

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 50° C., preferably at ambient temperature, for 24 to 52 hours, preferably 48 hours, in the presence of (i) 4-dodecybenzenesulfonic acid (DBSA), preferably present in an amount of 15-25 mol %, more preferably about 20 mol %, with respect to the intermediate of formula II;

to obtain an intermediate of formula I.

87. The process of item 1, wherein $R^1$ is hydrogen, $R^2$ is benzyl and $R^3$ is methyl;

the process comprises or consists the steps of:

(a) providing an intermediate of formula II, wherein $R^3$ is methyl;

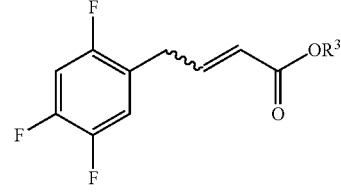

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 60° C., for 10 to 25 hours, preferably 18 hours, in the presence of (i) phosphotungstic acid, preferably present in an amount of 3-10 mol %, more preferably about 5 mol %, with respect to the intermediate of formula II;

to obtain an intermediate of formula I.

88. The process of item 1, wherein $R^1$ is hydrogen, $R^2$ is benzyl and $R^3$ is methyl;

the process comprises or consists the steps of:

(a) providing an intermediate of formula II, wherein $R^3$ is methyl;

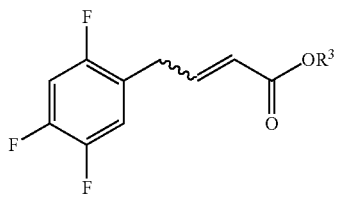

(II)

(b) reacting the intermediate of formula II with benzylamine present in an amount of 1.1 to 1.5 equivalents, preferably about 1.2 equivalents, with respect to the intermediate of formula II, without adding of solvents in step (a) and step (b) at 25° C. to 90° C., preferably at 60° C., for 10 to 25 hours, preferably 16 hours, in the presence of (i) sodium dodecylsulfate, preferably present in an amount of 10-30 mol %, more preferably about 20 mol %, with respect to the intermediate of formula II, to obtain an intermediate of formula I.

89. The process of item 1, wherein $R^1$ is hydrogen, $R^2$ is benzyl and $R^3$ is methyl;

the process comprises or consists the steps of:

(a) providing an intermediate of formula II, wherein $R^3$ is methyl;

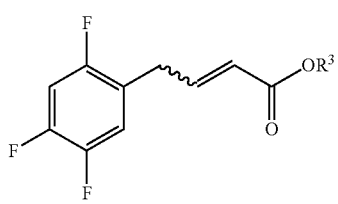

(II)

(b) reacting the intermediate of formula II with benzylamine present in an amount of 1.1 to 1.5 equivalents, preferably about 1.2 equivalents, with respect to the intermediate of formula II, without adding of solvents in the step (b) at 25° C. to 90° C., preferably at 60° C., for 10 to 25 hours, preferably 18 hours, in the presence of (i) cetyltrimethylammonium bromide, preferably present in an amount of 10-30 mol %, more preferably about 20 mol %, with respect to the intermediate of formula II, to obtain an intermediate of formula I.

90. The process of item 1, wherein $R^1$ is hydrogen, $R^2$ is O-benzyl and $R^3$ is methyl;

the process comprises or consists the steps of:

(a) providing an intermediate of formula II, wherein $R^3$ is methyl;

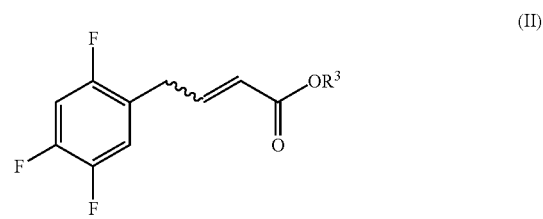

(II)

(b) reacting the intermediate of formula II with O-benzyl-hydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) 4-dodecybenzenesulfonic acid (DBSA), preferably present in an amount of 15-25 mol %, more preferably about 20 mol %, with respect to the intermediate of formula II;

to obtain an intermediate of formula I.

91. The process of item 1, wherein $R^1$ is hydrogen, $R^2$ is O-benzyl and $R^3$ is methyl;

the process comprises or consists the steps of:

(a) providing an intermediate of formula II, wherein $R^3$ is methyl;

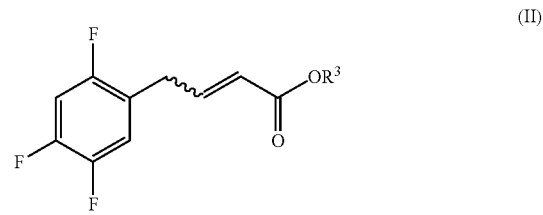

(II)

(b) reacting the intermediate of formula II with O-benzyl-hydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) 2,2,2-trifluoroethanol, preferably present in an amount of 1-15 equivalents, preferably about 3-12 equivalents, more preferably about 5 equivalents with respect to the intermediate of formula H;

to obtain an intermediate of formula I.

92. The process of item 1, wherein $R^1$ is hydrogen, $R^2$ is O-benzyl and $R^3$ is methyl; and the process comprises or consists the steps of:

(a) providing an intermediate of formula II, wherein $R^3$ is methyl;

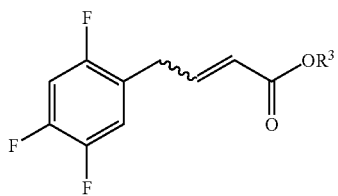

(II)

(b) reacting the intermediate of formula II with O-benzyl-hydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) scandium(III) triflate, preferably present in an amount of 1-30 mol %, preferably about 5-25 mol %, more preferably about 20 mol %, with respect to the intermediate of formula II; and (ii) sodium dodecylsulfate, present in an amount of 1-30 mol %, preferably about 5-25 mol %, more preferably about 20 mol %, with respect to the intermediate of II;

to obtain an intermediate of formula I.

93. The process of item 1, wherein $R^1$ is hydrogen, $R^2$ is O-benzyl and $R^3$ is methyl; and the process comprises or consists the steps of:

(a) providing an intermediate of formula II, wherein $R^3$ is methyl;

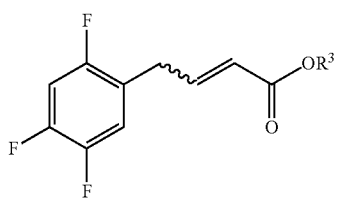

(II)

(b) reacting the intermediate of formula II with O-benzyl-hydroxylamine present in an amount of 1.1 to 2.0 equivalents, preferably about 1.4 equivalents, with respect to the intermediate of formula II, in water at 50° C. to 90° C., preferably at 60° C., for 10 to 30 hours, preferably 24 hours, in the presence of (i) 2,2,2-trifluoroethanol, present in an amount of 1-15 equivalents, preferably about 3-12 equivalents, more preferably about 5 equivalents, with respect to the intermediate of formula II; and (ii) sodium dodecylsulfate, preferably present in an amount of 1-30 mol %, preferably about 5-20 mol %, more preferably about 8 mol %, with respect to the intermediate of II;

to obtain an intermediate of formula I.

94. Use of a process of any of preceding items in a process for the preparation of anti-diabetic agents, in particular (R)-3-amino-1-[3-(trifluormethyl)-5,6,7,8-tetrahydro[1,2,4]triazol[4,3-a]pyrazin-7-yl]-4-(2,4,5-trifluorphenyl)butan-1-on.

The invention claimed is:

1. A process for the preparation of an intermediate of formula I,

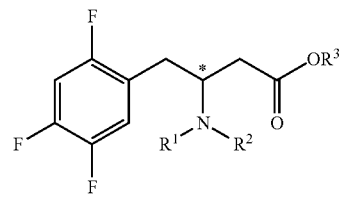

(I)

wherein the stereogenic center marked with an * is either in (R)- or (S)-configuration at marked center, or it is in racemic form, and wherein $R^1$ and $R^2$ are identical or different, and are independently selected from (i) hydrogen;

(ii) alkyl residues optionally chiral, having from 1 to 12 carbon atoms, wherein the alkyl residues are optionally aryl and/or aryloxy substituted;

(iii) alkyloxy residues optionally chiral, having from 1 to 12 carbon atoms, wherein the alkyloxy residues are optionally aryl substituted;

(iv) aryl residues optionally chiral, having from 6 to 24 carbon atoms, wherein the aryl residues are optionally alkyl and/or alkyloxy substituted;

(v) aryloxy residues optionally chiral, having from 6 to 24 carbon atoms, wherein the aryloxy residues are optionally alkyl substituted;

(vi) benzyl;

(vii) alkaloyl residues optionally chiral, having from 2 to 13 carbon atoms, wherein the alkaloyl residues are optionally aryl substituted;

(viii) aroyl residues optionally chiral, having from 7 to 25 carbon atoms, wherein the aryloxy residues are optionally alkyl substituted;

(ix) alkoxycarbonyl residues optionally chiral, having from 2 to 13 carbon atoms;

(x) aryloxycarbonyl residues optionally chiral, having from 7 to 25 carbon atoms;

(xi) tosyl;

(xii) silyl residues optionally chiral, having from 3 to 15 carbon atoms; and (xiii) silyloxy residues optionally chiral, having from 3 to 15 carbon atoms;

wherein $R^3$ is selected from alkyl residues having from 1 to 6 carbon atoms;

the process comprising the steps of:

(a) providing an intermediate of formula II,

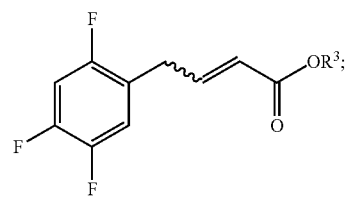

(II)

(b) reacting the intermediate of formula II with an amine of formula III,

HNR¹R²            (III)

wherein R¹ and R² are as defined above, in the presence of a catalyst or promoter or a combination thereof, in a protic solvent; or in a mixture of protic solvents, wherein the mixture comprises water;

wherein the catalyst is selected from Brønsted acids, amino acids, thioureas, and Cinchona alkaloids, and the promoter is selected from fluorinated alcohols and surfactants, to obtain an intermediate of formula I.

2. The process of claim 1, wherein in step (b) the solvent is selected from the group consisting of water, methanol, ethanol, iso-propanol, tert-butanol, trifluoroethanol, hexafluoro-2-propanol, amyl alcohol and any combination thereof.

3. The process of claim 1, wherein step (b) is carried out in water.

4. The process of claim 1, wherein step (b) is carried out at a temperature of 20° C. to 100° C.

5. The process of claim 1, wherein the intermediate of formula I is selected from the group consisting of

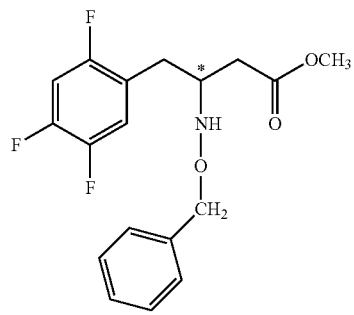

(Ia)

(Ib)

(Ic)

(Id)

-continued

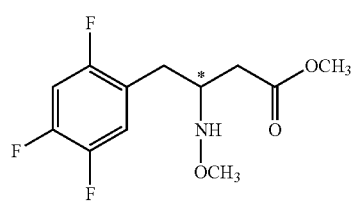

(Ie)

(If)

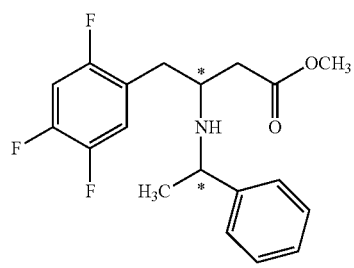

(Ig)

(Ih)

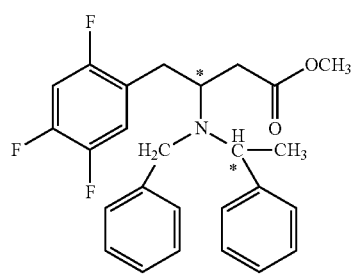

(Ii)

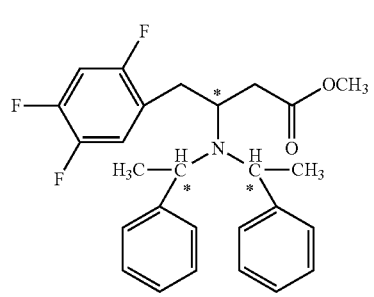

-continued

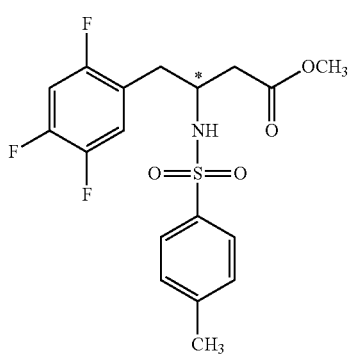
(Ij)

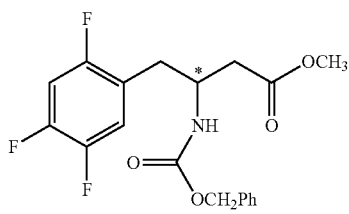
(Ik)

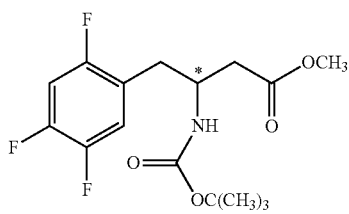
(Il)

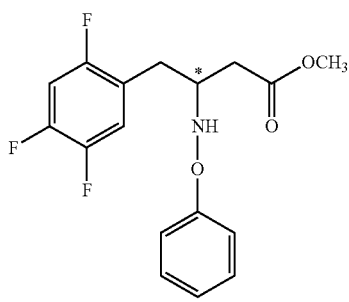
(Im)

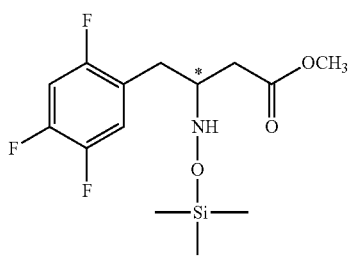
(In)

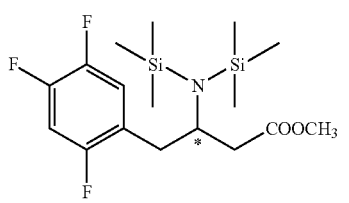
(Io)

wherein the stereogenic center marked with an * is either in (R)- or (S)-configuration at marked center, or it is in racemic form.

6. The process of claim 1, wherein step (b) is an acid catalyzed process.

7. The process of claim 1, wherein in step (b) the acid is a Brønsted acid is selected from the group consisting of 4-dodecylbenzenesulfonicacid (DBSA), phosphotungstic acid, Nafion-H, trifluoromethanesulfonic acid (HOTf), phosphomolybdic acid, methanesulfonic acid, p-toluenesulfonic acid (PTSA), chlorsulfonic acid 2,5-dinitrobenzenesulfonic acid (DNBSA), sulfuric acid, polystyrenesulfonic acid (PSSA), boric acid, phenylboric acid, and any combination thereof.

8. The process of claim 1, wherein in step (b) the amino acid is selected from the group consisting of pyroglutamic acid, threonine, aspartic acid, proline derivatives, and any combination thereof; the thiourea is selected from the group consisting of N-[3,5-bis(trifluoromethyl)phenyl]-N'-[6'-methoxy-9-cinchonanyl]thiourea, 2-[[3,5-bis(trifluoromethyl)phenyl]thioureido]-N-benzyl-N,3,3-trimethylbutanamide, and any combination thereof; and the cinchona alkaloid is selected from the group consisting of quinidine, 6'-methoxycinchonan-9-amine trihydrochloride and any combination thereof.

9. The process of claim 1, wherein in step (b) the fluorinated alcohols are selected from the group consisting of trifluoroethanol, hexafluoro-2-propanol, and any combination thereof.

10. The process of claim 1, wherein in step (b) the surfactants are selected from the group consisting of ionic surfactants, nonionic surfactants, and the combination thereof, wherein the ionic surfactants are selected from the group consisting of sodium dodecyl sulfate, cetyltrimethylammonium bromide, and any combination thereof, and the nonionic surfactants are selected from the croup consisting of D-a-tocopherol polyethylene glycol succinate and polyoxyethanyl-α-tocopheryl sebacate, and any combination thereof.

11. A method of preparing an anti-diabetic agent, the method comprising obtaining the compound (R)-3-amino-1-[3-(trifluormethyl)-5,6,7,8-tetrahydro[1,2,4]triazol[4,3-a]pyrazin-7-yl]-4-(2,4,5-trifluorphenyl)butan-1-on from the process according to claim 1, and combining said compound with a pharmaceutically acceptable excipient.

12. A process for the preparation of an intermediate of formula I,

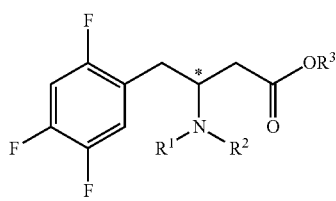
(I)

wherein the stereogenic center marked with an * is either in (R)- or (S)-configuration at marked center, or it is in racemic form, and wherein $R^1$ and $R^2$ are identical or different, and are independently selected from (i) hydrogen;

(ii) alkyl residues optionally chiral, having from 1 to 12 carbon atoms, wherein the alkyl residues are optionally aryl and/or aryloxy substituted;

(iii) alkyloxy residues optionally chiral, having from 1 to 12 carbon atoms, wherein the alkyloxy residues are optionally aryl substituted;

(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted;
(ix) alkoxycarbonyl residues optionally chiral, having from 2 to 13 carbon atoms;
(x) aryloxycarbonyl residues optionally chiral, having from 7 to 25 carbon atoms;
(xi) tosyl;
(xii) silyl residues optionally chiral, having from 3 to 15 carbon atoms; and
(xiii) silyloxy residues optionally chiral, having from 3 to 15 carbon atoms;
wherein $R^3$ is selected from alkyl residues having from 1 to 6 carbon atoms;
the process comprising the steps of:
(a) providing an intermediate of formula II,

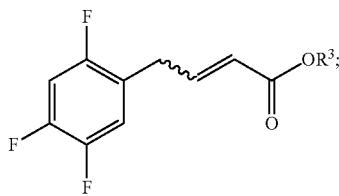

(b) reacting the intermediate of formula II with an amine of formula III,

HNR$^1$R$^2$ (III)

wherein $R^1$ and $R^2$ areas defined above, in a protic solvent; or in a mixture of protic solvents, wherein the mixture comprises water; or without adding of solvents in step (b),
wherein step (b) is an acid catalyzed process, and wherein in step (b) the acid is a Brønsted acid, selected from the group consisting of 4-dodecylbenzenesulfonicacid (DBSA), phosphotungstic acid, Nafion-H, trifluoromethanesulfonic acid (HOTf), phosphomolybdic acid, methanesulfonic acid, p-toluenesulfonic acid (PTSA), chlorsulfonic acid 2,5-dinitrobenzenesulfonic acid (DNBSA), sulfuric acid, polystyrenesulfonic acid (PSSA), boric acid, phenylboric acid, and any combination thereof;
to obtain an intermediate of formula I.

13. A process for the preparation of an intermediate of formula I,

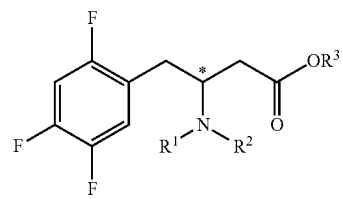

wherein the stereogenic center marked with an * is either in (R)- or (S)-configuration at marked center, or it is in racemic form, and
wherein $R^1$ and $R^2$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted;
(ix) alkoxycarbonyl residues optionally chiral, having from 2 to 13 carbon atoms;
(x) aryloxycarbonyl residues optionally chiral, having from 7 to 25 carbon atoms;
(xi) tosyl;
(xii) silyl residues optionally chiral, having from 3 to 15 carbon atoms; and
(xiii) silyloxy residues optionally chiral, having from 3 to 15 carbon atoms;
wherein $R^3$ is selected from alkyl residues having from 1 to 6 carbon atoms;
the process comprising the steps of:
(a) providing an intermediate of formula II,

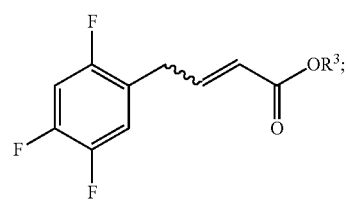

(b) reacting the intermediate of formula II with an amine of formula III,

HNR$^1$R$^2$ (III)

wherein $R^1$ and $R^2$ areas defined above, in a protic solvent; or in a mixture of protic solvents, wherein the mixture comprises water; or without adding of solvents in step (b), and wherein step (b) is carried out in the presence of a promoter, which is a fluorinated alcohol selected from the group consisting of trifluoroethanol, hexafluoro-2-propanol, and any combination thereof;

to obtain an intermediate of formula I.

* * * * *